(12) United States Patent
Marette et al.

(10) Patent No.: US 9,782,379 B2
(45) Date of Patent: Oct. 10, 2017

(54) USE OF PROTECTIN DX FOR THE STIMULATION OF MUSCULAR IL-6 SECRETION

(71) Applicant: Universite Laval, Quebec (CA)

(72) Inventors: Andre Marette, St-Nicolas (CA); Philip J. White, Durham, NC (US)

(73) Assignee: Universite Laval, Quebec (CA)

( * ) Notice: Subject to any disclaimer, the term of this patent is extended or adjusted under 35 U.S.C. 154(b) by 0 days.

(21) Appl. No.: 14/763,080

(22) PCT Filed: Jan. 23, 2014

(86) PCT No.: PCT/CA2014/000047
§ 371 (c)(1),
(2) Date: Jul. 23, 2015

(87) PCT Pub. No.: WO2014/113875
PCT Pub. Date: Jul. 31, 2014

(65) Prior Publication Data
US 2015/0352069 A1    Dec. 10, 2015

Related U.S. Application Data

(60) Provisional application No. 61/756,683, filed on Jan. 25, 2013.

(51) Int. Cl.
| | | |
|---|---|---|
| A61K 31/20 | (2006.01) | |
| A01N 37/00 | (2006.01) | |
| A61K 31/202 | (2006.01) | |
| A61K 38/17 | (2006.01) | |

(52) U.S. Cl.
CPC ........ *A61K 31/202* (2013.01); *A61K 38/1709* (2013.01)

(58) Field of Classification Search
CPC .......................... A61K 31/202; A61K 38/1709
USPC ....................................................... 514/560
See application file for complete search history.

(56) References Cited

U.S. PATENT DOCUMENTS

| | | | | |
|---|---|---|---|---|
| 8,273,792 B2 * | 9/2012 | Serhan | .................... | C07C 59/42 514/549 |
| 2009/0156673 A1 * | 6/2009 | Serhan | .................... | C07C 59/42 514/549 |

FOREIGN PATENT DOCUMENTS

WO    2008058274 A2    5/2008

OTHER PUBLICATIONS

PCT International Search Report and Written Opinion for PCT Application No. PCT/CA2014/000047 mailed Apr. 16, 2014 (10 pages).
Chen et al., "Poxytrins, a Class of Oxygenated Products from Polyunsaturated Fatty Acids, Potently Inhibit Blood Platelet Aggregation," The FASEB Journal, 2011, vol. 25, pp. 382-388.
Serhan et al., "Anti-Inflammatory Actions of Neuroprotectin D1/Protectin D1 and Its Natural Stereoisomers: Assignments of Dihydroxy-Containing Docosatrienes," The Journal of Immunology, 2006, vol. 176, pp. 1848-1859.
Abstracts / Chemistry and Physics of Lipids, 1605, (2009) S1-S17.
Merched et al., "Atherosclerosis: evidence for impairment of resolution of vascular inflammation governed by specific lipid mediators", The FASEB Journal, 2016, 22(10):3595-3606.
Chen et al., "Full characterization of PDX, a neuroprotectin/protectin D1 isomer, which inhibits blood platelet aggregation", FEBS Letters, 2009, 583:3478-3484.
Supplementary European Search Report for Application No. 14743766 dated Oct. 4, 2016, 3 pages.

* cited by examiner

*Primary Examiner* — My-Chau T Tran
(74) *Attorney, Agent, or Firm* — Eversheds Sutherland (US) LLP

(57) ABSTRACT

The present invention provides a method for the stimulation of secretion or expression of muscular IL-6 in a subject with the administration of Protectin DX (PDX). Particularly, the increase in circulating levels of IL-6 originating from the subject muscles is useful for regulating blood glucose and suppressing lipid-induced inflammation and other related inflammatory conditions such as insulin resistance, metabolic syndrome, type-2 diabetes, hypertension and cardiovascular diseases. Alternatively, the increase in muscular IL-6 expression in a subject may also be useful for increasing energy supply during exercise, or facilitating muscular recovery after strenuous effort.

4 Claims, 21 Drawing Sheets

*Figure 2 (con'd)*
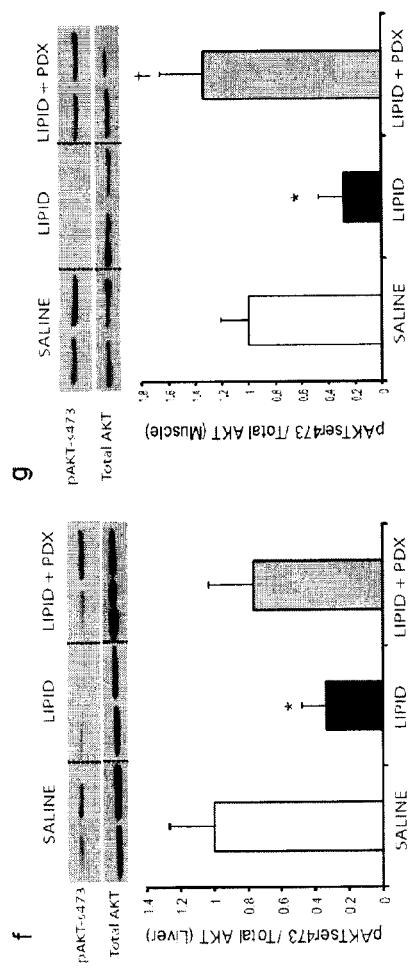
*Figure 3*
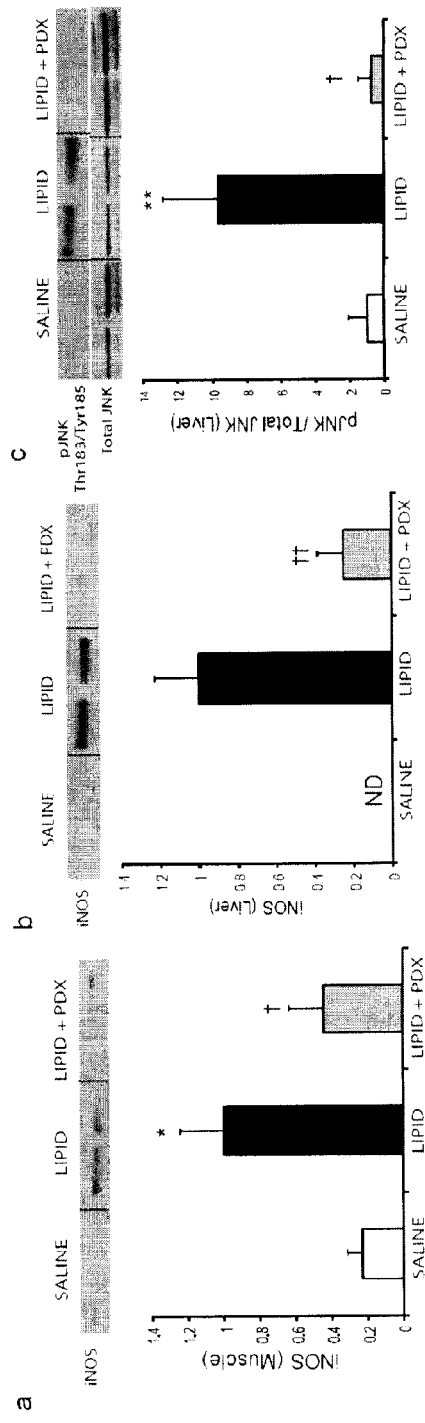

Chronic PDX treatment in db/db mice

- Surgery on 18 wks old mice.
- 5 days treatment with 2µg of PDX (Santa Cruz).
- On the day of the experiments, animal received 2x2µg of PDX.
- Clamp or IVGTT was performed.
- Tissues were sampled, frozen and kept at -80°C:
  - iWAT, eWAT, gastrocnemius muscle, liver, pancreas.

Hyperinsulinemic-isoglycemic clamp procedure

USE OF PROTECTIN DX FOR THE STIMULATION OF MUSCULAR IL-6 SECRETION

CROSS REFERENCE TO RELATED APPLICATIONS

This application claims the priority benefit of PCT/CA2014/000047 filed on Jan. 23, 2014 and U.S. Provisional Application No. 61/756,683 filed on Jan. 25, 2013. The contents of these applications are hereby incorporated by reference in their entirety.

FIELD OF THE INVENTION

The present invention relates to a method for the stimulation of secretion and expression of muscular IL-6 in a subject comprising the administration of Protectin DX (PDX). Particularly, the increase in circulating levels of IL-6 originating from the subject muscles is useful for suppressing lipid-induced inflammation and other related inflammatory conditions such as insulin resistance, metabolic syndrome and type-2 diabetes. Method for regulating blood glucose metabolism is also provided. Alternatively, the increase in muscular IL-6 expression in a subject may also be useful for increasing energy supply during exercise, or facilitating muscular recovery after strenuous effort.

BACKGROUND OF THE INVENTION

It is now widely accepted that inflammation is a key component of the etiology of obesity-linked insulin resistance leading the way to type 2 diabetes mellitus (T2DM) (Wellen and Hotamisligil, 2005; White and Marette, 2008). Novel anti-inflammatory compounds are therefore of great interest to the field. The enzymatic oxidation of omega-3 (ω-3) polyunsaturated fatty acids (PUFA) yields multiple families of bioactive lipids, which include the resolvins, protectins and maresins (Norling and Serhan, 2010). These novel lipid mediators possess potent anti-inflammatory activity owing to their role in the active termination of endogenous inflammation; however, their therapeutic potential for the treatment of metabolic disorders such as insulin resistance remains to be demonstrated.

Using fat-1 transgenic mice that are characterized by elevated tissue ω-3 content (Kang et al., 2004), we recently demonstrated that greater endogenous biosynthesis of protectin D1 in adipose tissue and skeletal muscle of high fat fed obese mice is associated with an improved global resolution capacity, reduced inflammation and protection from insulin resistance (White et al., 2010).

Protectin D1 (PD1), identified as 10R,17S-dihydroxy-docosa-4Z,7Z,11E,13E,15Z,19Z-hexaenoic acid, is the most studied member of the protectin family (Serhan et al., 2006). PD1 is derived from 12/15-lipoxygenase mediated oxygenation of docosahexaenoic acid (DHA; 22:6 n-3) followed by epoxidation and reduction of the 17S-hydroperoxy DHA intermediate (Serhan et al., 2006). A natural stereoisomer of PD1, 10S,17S-dihydroxy-docosa-4Z,7Z,11E,13Z,15E,19Z-hexaenoic acid, first described as compound I (Serhan et al., 2006) and recently designated Protectin DX (PDX) (Chen et al., 2009) is also present in vivo. PDX is produced via sequential lipoxygenation of DHA and differs from PD1 with respect to the double bond geometry of carbons 13 and 15 as well as the position of the C-10 hydroxyl (Chen et al., 2009; Serhan et al., 2006). PDX is found alongside PD1 in murine inflammatory exudates and may also be produced by human neutrophils exposed to DHA, albeit to a lesser extent than PD1 (Serhan et al., 2006). To the best of our knowledge the influence of protectins on insulin sensitivity and glucose metabolism has not yet been examined.

The prior art is replete with data indicating that IL-6 is decreased following the administration of molecules from the Resolvin/Protectin families (Schwab et al. 2007; Aksam et al. 2008; Hawort et al. 2008, Liao et al. 2012; Das 2012).

Herein is provided a first evidence of the therapeutic potential of PDX for lipid-induced inflammation and insulin resistance. Importantly, we reveal an unanticipated mechanism of action whereby PDX enhances both hepatic and peripheral glucose metabolism in vivo by increasing the prototypic myokine IL-6.

SUMMARY OF THE INVENTION

The invention therefore provides use of Protectin DX (PDX) for the stimulation of IL-6 muscular secretion in a subject.

In a first aspect, the present invention provides use of PDX for the treatment of a condition treated by the secretion of muscular IL-6 in a subject in need thereof.

In a further aspect, the invention provides use of PDX for the manufacture of a medication for the treatment of a condition treated by the secretion of muscular IL-6 in a subject in need thereof.

In a further aspect, there is provided use of Protectin DX (PDX) for the manufacture of a formulation for the recovery of exercise recovery or muscular fatigue.

In a further aspect, there is provided use of Protectin DX (PDX) for the manufacture of a formulation for increasing body or skeletal muscle glucose absorption.

In a further aspect, there is provided use of Protectin DX for the manufacture of a formulation for increasing energy supply during exercise comprising secretion of muscular IL-6.

In a further aspect, there is provided use of Protectin DX (PDX) for the manufacture of a formulation for stimulating muscular IL-6 secretion during strenuous effort.

In a further aspect, there is provided a method for the treatment of a condition treated by the secretion of muscular IL-6 comprising the administration of Protectin DX (PDX) in a subject suffering therefrom.

In an alternative aspect, there is provided a use or a method for lowering blood glucose in a subject in need thereof comprising the administration of PDX to said subject.

In a further aspect, provided is a use or a method for increasing body or skeletal muscle glucose absorption in a subject in need thereof comprising the administration of PDX to said subject.

Still, in a further aspect, the invention provides a use or a method for increasing energy supply during exercise comprising secretion of muscular IL-6 comprising the administration of PDX in a subject performing said exercise.

Alternatively, the invention provides a use or a method for stimulating muscular IL-6 secretion during strenuous effort, comprising the administration of PDX in a subject performing said effort.

DETAILED DESCRIPTION OF THE INVENTION

Description of the Figures

Figure 1:
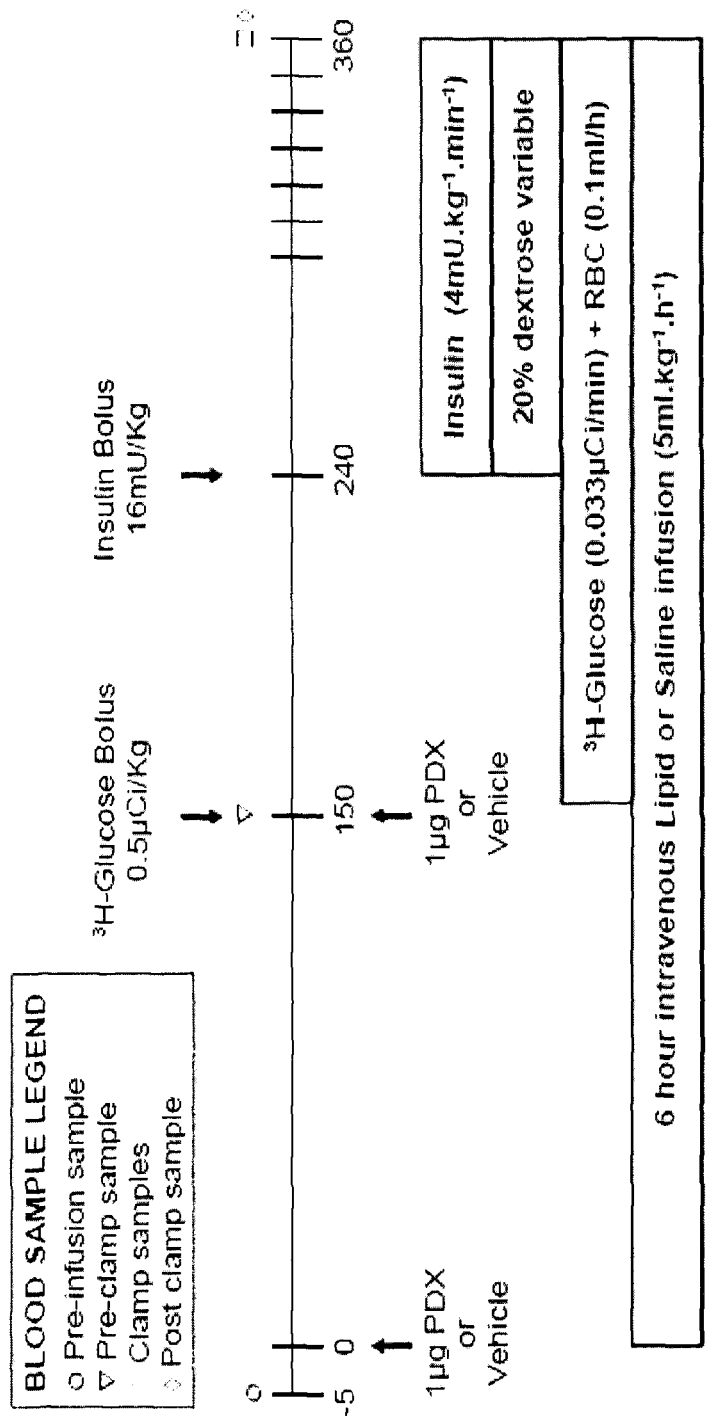
FIG. 1. Schematic representation of the hyperinsulinemic-euglycemic clamp protocol FIGS. 2a-2g. PDX prevents lipid-induced insulin resistance FIGS. 3a-3k. PDX inhibits lipid-induced inflammation FIG. 4. PDX suppresses lipid-induced secretion of CCL2/MCP-1, CCL5/RANTES, TNFg, IL-2, IL-10, iNOS and JNK as well as IL-6 production in macrophages FIGS. 5a-5n. PDX stimulates skeletal muscle IL-6 expression FIG. 6. PDX does not induce IL-6 mRNA expression in cultured macrophages FIGS. 7a-7j. IL-6 is reguired for the insulin sensitizing actions of PDX FIGS. 8a-8d. Role of IL-6 in PDX mediated activation of AMPK and STAT-3
Figure 2:
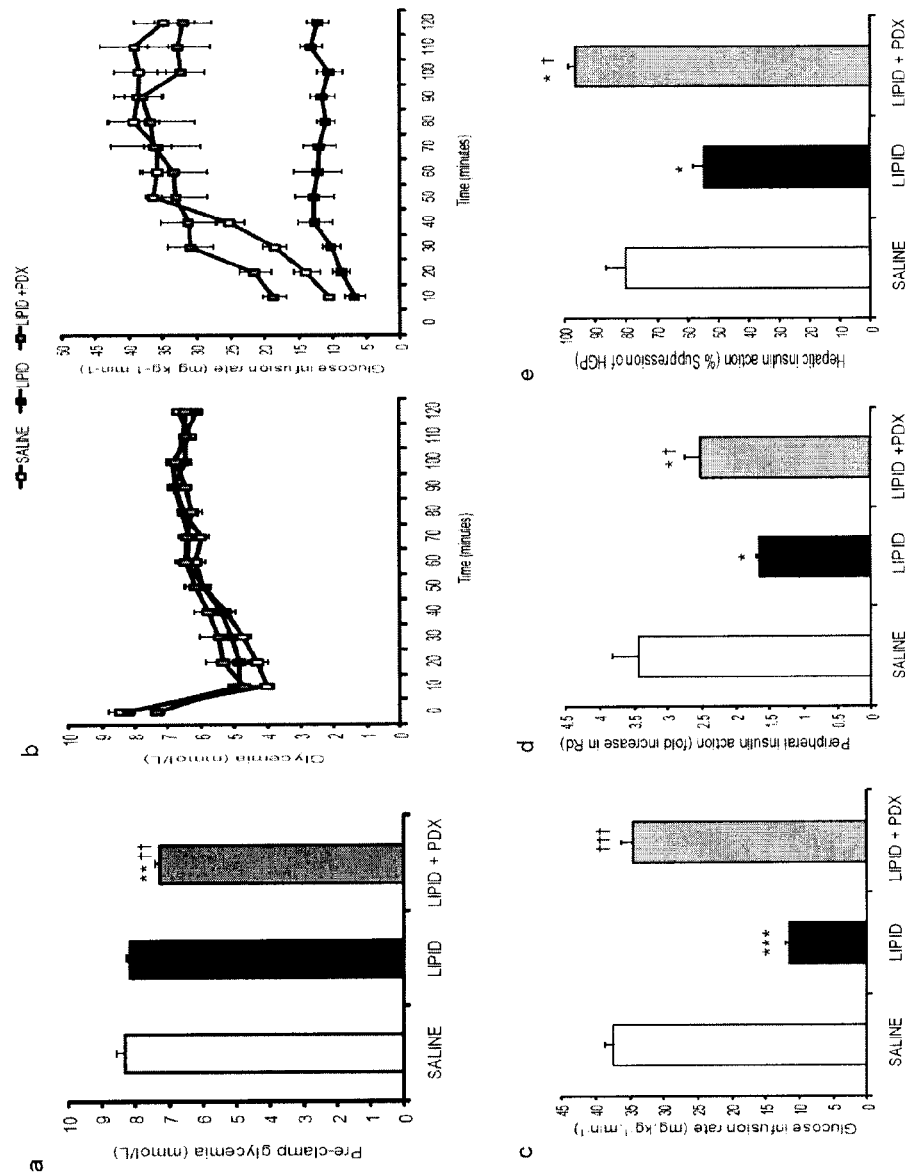

FIG. 1. Schematic representation of the hyperinsulinemic-euglycemic clamp protocol FIG. 2. PDX prevents lipid-induced insulin resistance Pre-clamp glycemia is shown in panel a. (b) Glycemia and glucose infusion rate (GIR) during the hyperinsulinemic-euglycemic clamp. (c) Mean GIR for last 60 min of clamp is reduced by lipid-infusion but restored by PDX administration (d) Peripheral insulin action expressed as fold increase in Rd during the clamp is improved in PDX treated mice (e) PDX markedly improved hepatic insulin action expressed as percent suppression of hepatic glucose production (HGP) during the clamp (f-g) Immunoblots for pAKTser473, total AKT in gastrocnemius muscle and liver show that PDX maintains insulin signal transduction to Akt. Quantification of densitometry analyses are shown below the representative gels. Lanes were run on the same gel but were noncontiguous. All data are mean±SEM, n=6, ND not detected, *$P<0.05$, $P<0.01$, *$P<0.001$ vs Saline; †$P<0.05$, ††$P<0.01$, †††$P<0.001$ vs Lipid. See also Supplementary FIG. 1 for study design.

Figure 3:
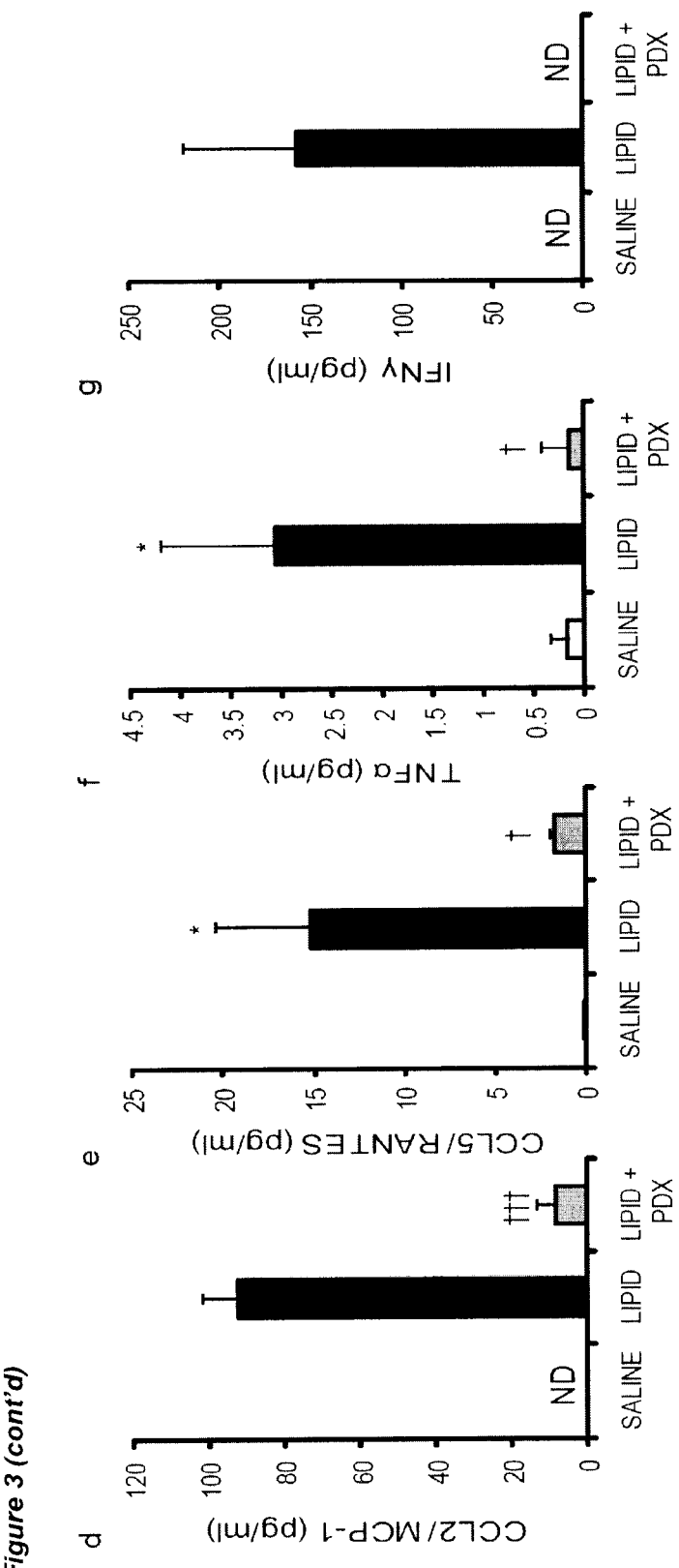
Figure 3:
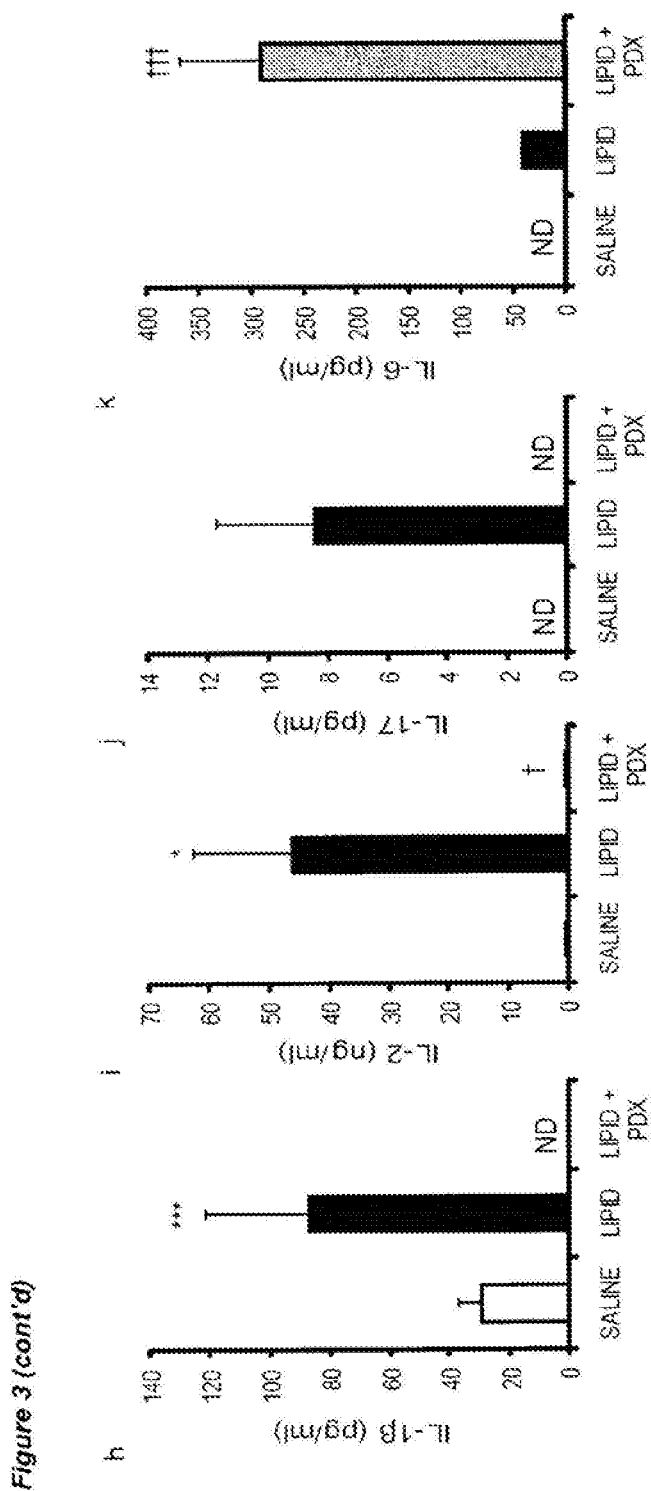

FIG. 3. PDX inhibits lipid-induced inflammation

Immunoblots for iNOS, pJNKthr183/tyr185, and total JNK reveal that PDX blunts lipid-mediated iNOS induction in skeletal muscle (a) and liver (b) as well as JNK activation in liver (c). Quantification of densitometry analyses are shown below the representative gels. Lanes were run on the same gel but were noncontiguous. PDX administration also prevented lipid-induced elevations in plasma chemokines (d-e) as well as Th1 (f-i) and Th17 (j) cytokines during the paired lipid infusion hyperinsulinemic-euglycemic clamp. PDX also provoked an increase in IL-6 (k). All data are mean±SEM, n=6, ND not detected, *$P<0.05$, ***$P<0.001$ vs Saline; †$P<0.05$, †††$P<0.001$ vs Lipid.

Figure 4:
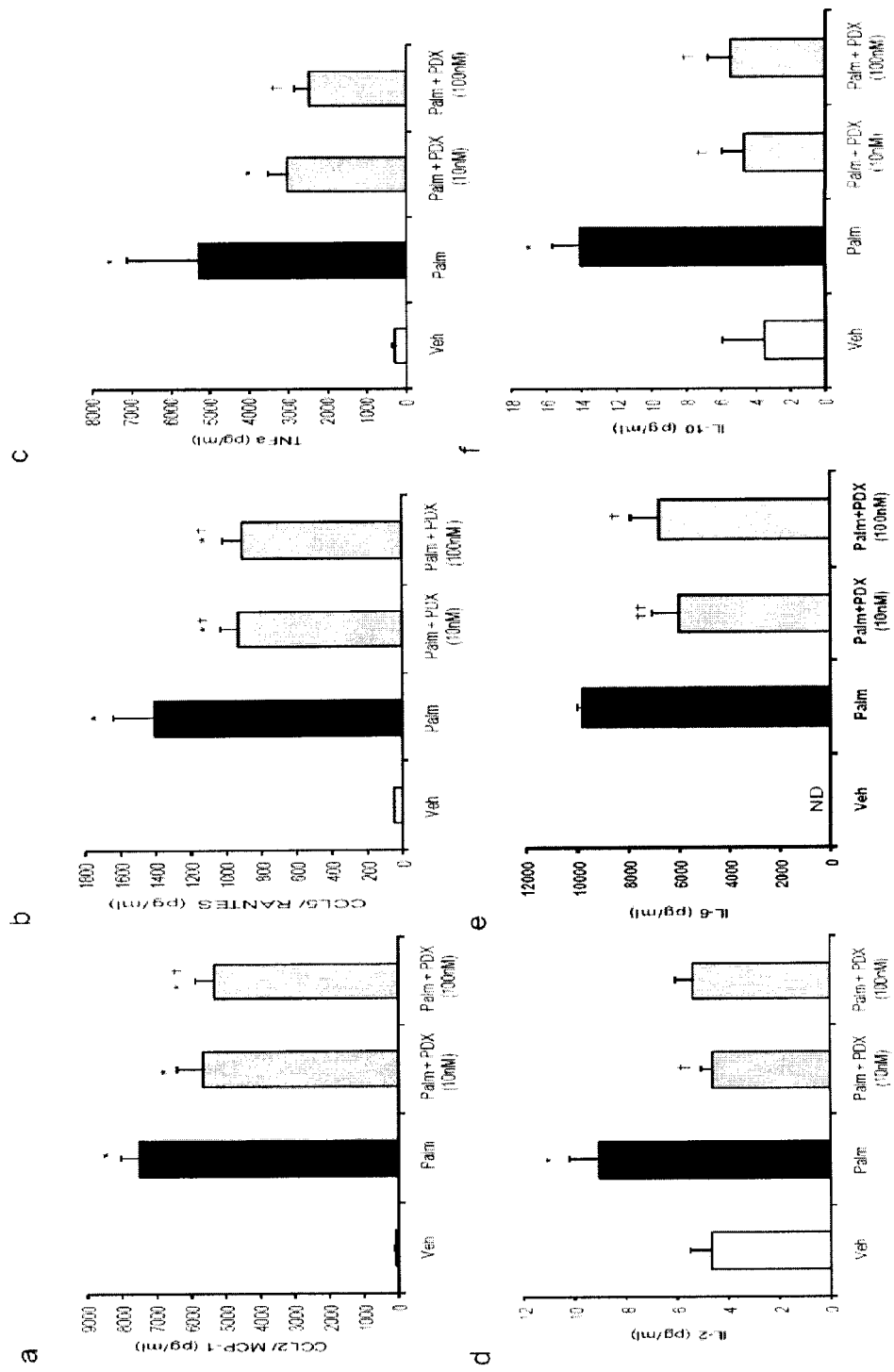
Figure 4:
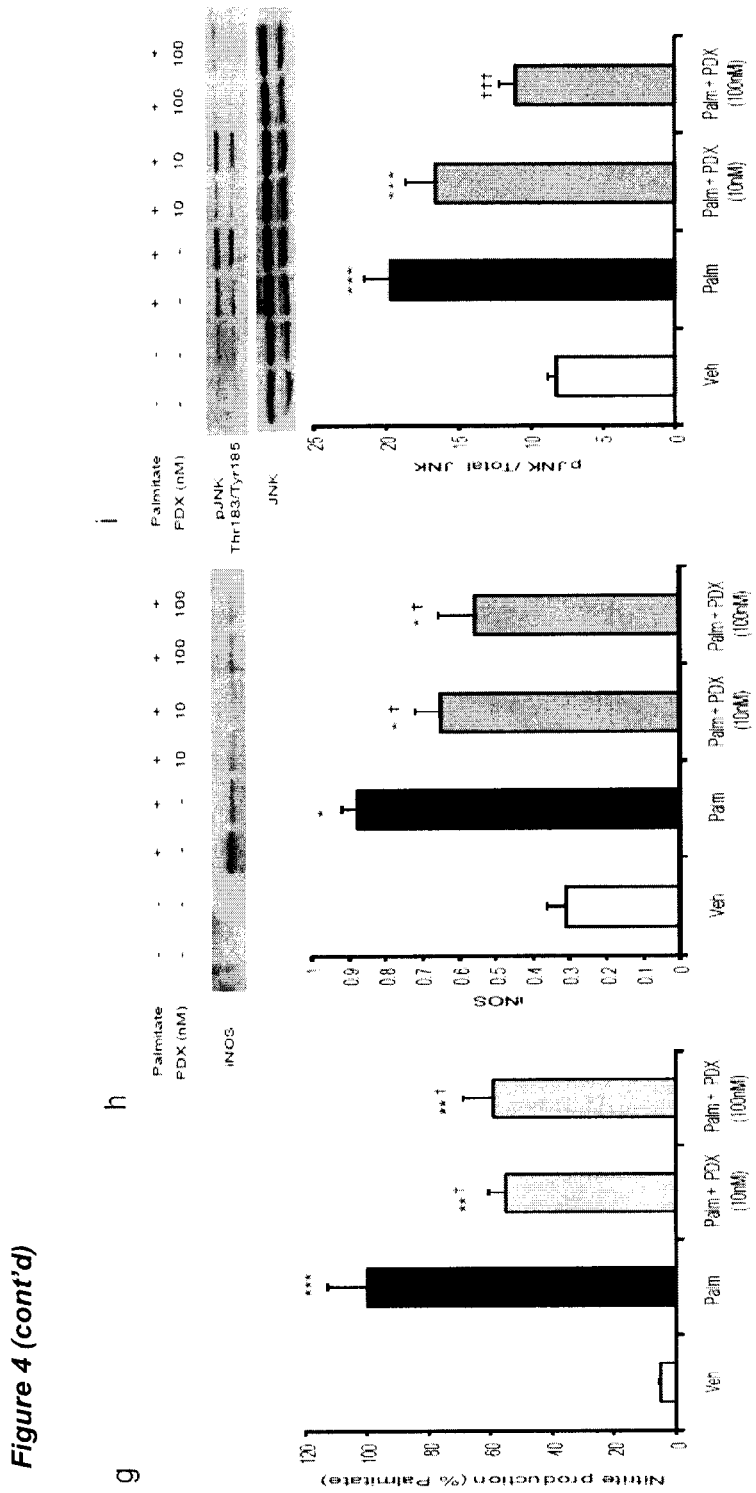
Figure 5:
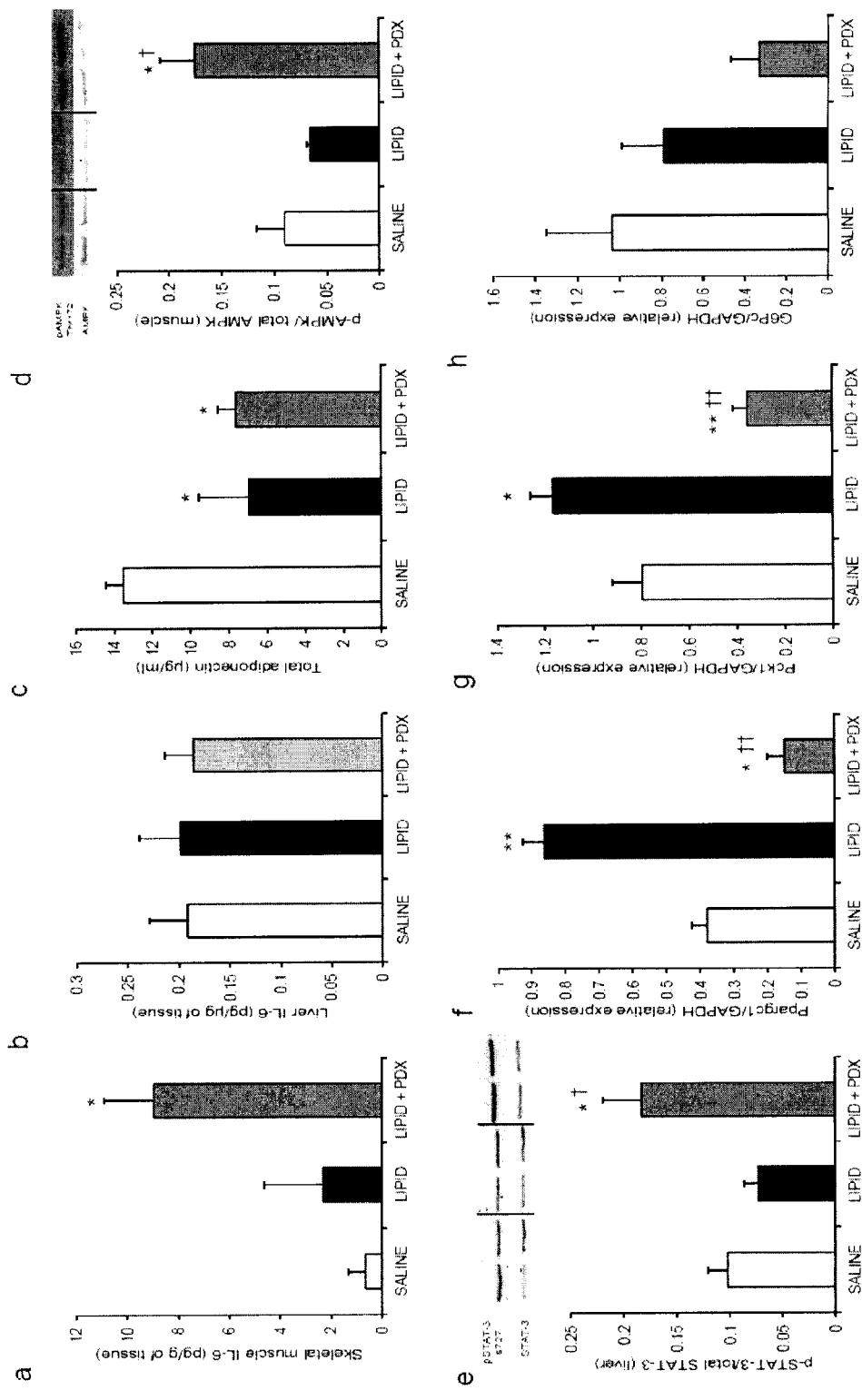
Figure 5:
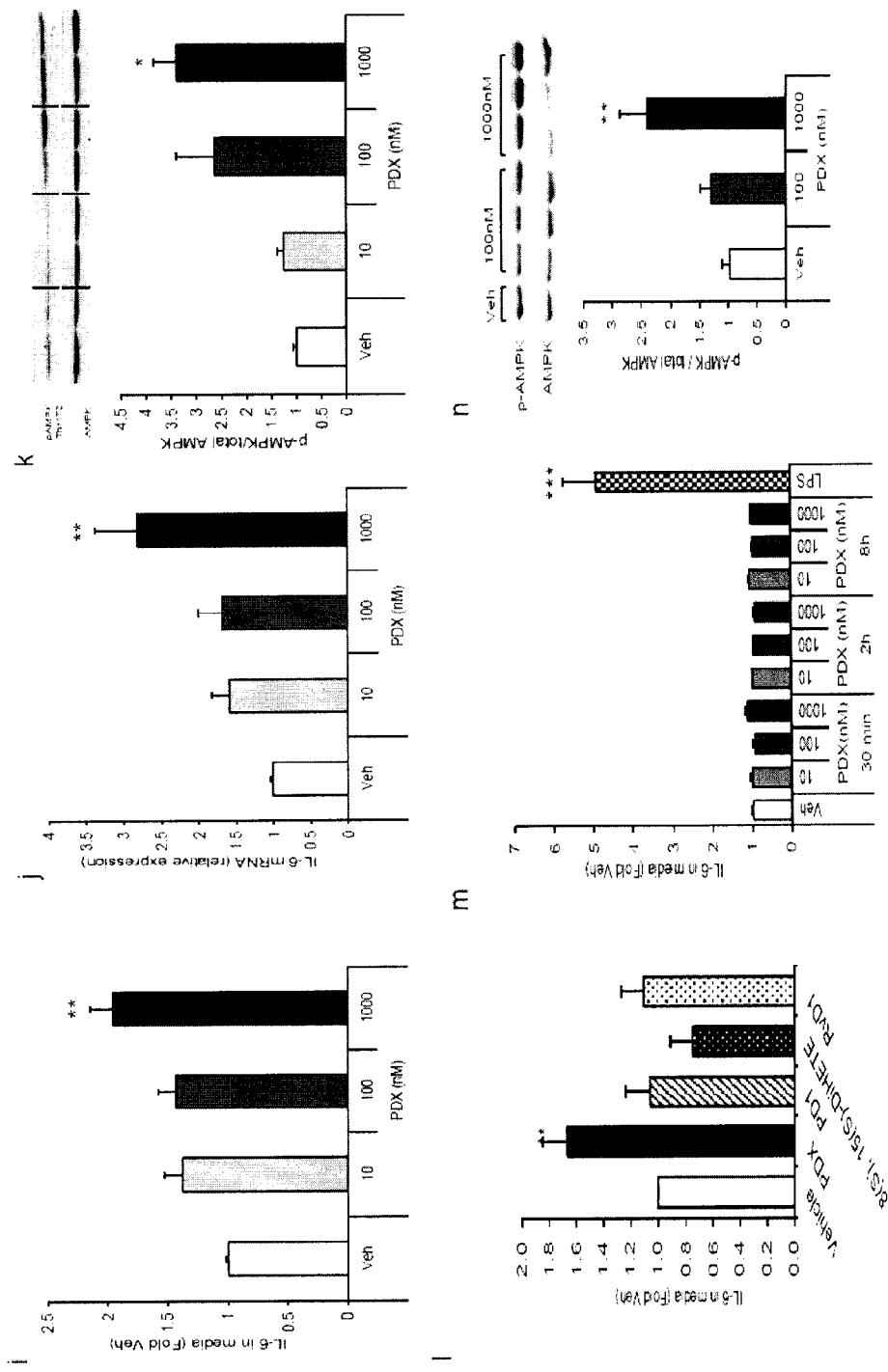

FIG. 4. PDX suppresses lipid-induced secretion of CCL2/MCP-1, CCL5/RANTES, TNFα, IL-2, IL-10, iNOS and JNK as well as IL-6 production in macrophages FIG. 5. PDX stimulates skeletal muscle IL-6 expression (a-b) Skeletal muscle and liver IL-6 protein expression. (c) Total plasma adiponectin. (d) Immunoblots for pAMPK thr172 and total AMPK in skeletal muscle. (e) Immunoblots for pSTAT-3 ser727 and total STAT-3 in liver. Quantification of densitometry analyses for immunoblots are shown below the representative gels. In each case lanes were run on the same gel but were noncontiguous. (f-h) Relative mRNA expression for Ppargc1, Pck1 and G6Pc in liver. All genes were normalized to GAPDH using the delta delta CT method. All data are mean±SEM, n=6, *$P<0.05$, **$P<0.01$ vs Saline; †$P<0.05$, ††$P<0.01$ vs Lipid. (i) IL-6 in media of C2C12 myotubes exposed to PDX for 2 h. (j) IL-6 mRNA expression in C2C12 myotubes exposed to PDX for 2 h. (k) Immunoblots for pAMPK thr172 and total AMPK in C2C12 myotubes exposed to PDX for 2 h. Quantification of densitometry analyses for immunoblots are shown below the representative gels. Lanes were run on the same gel but were noncontiguous. Data are mean±SEM of three independent experiments. *$P<0.05$, $P<0.01$ vs vehicle. (I) IL-6 in media of C2C12 myotubes exposed to Veh, or 100 nM of PDX, PD1, 8(S),15(s)-DiHETE, or RvD1. Data are mean±SEM of three independent experiments. $P<0.01$ vs vehicle. (m) IL-6 in media of J77A4 macrophages treated with Veh, LPS, or PDX (10, 100, or 1000 nM) for 30 min, 2 h and 8 h. (n) Immunoblots for pAMPK thr172 and total AMPK in C2C12 myotubes exposed to PDX for 2h. Quantification of densitometry analyses for immunoblots are shown below the representative gels. Data are mean±SEM of three independent experiments. **$P<0.01$ vs vehicle.

Figure 6:
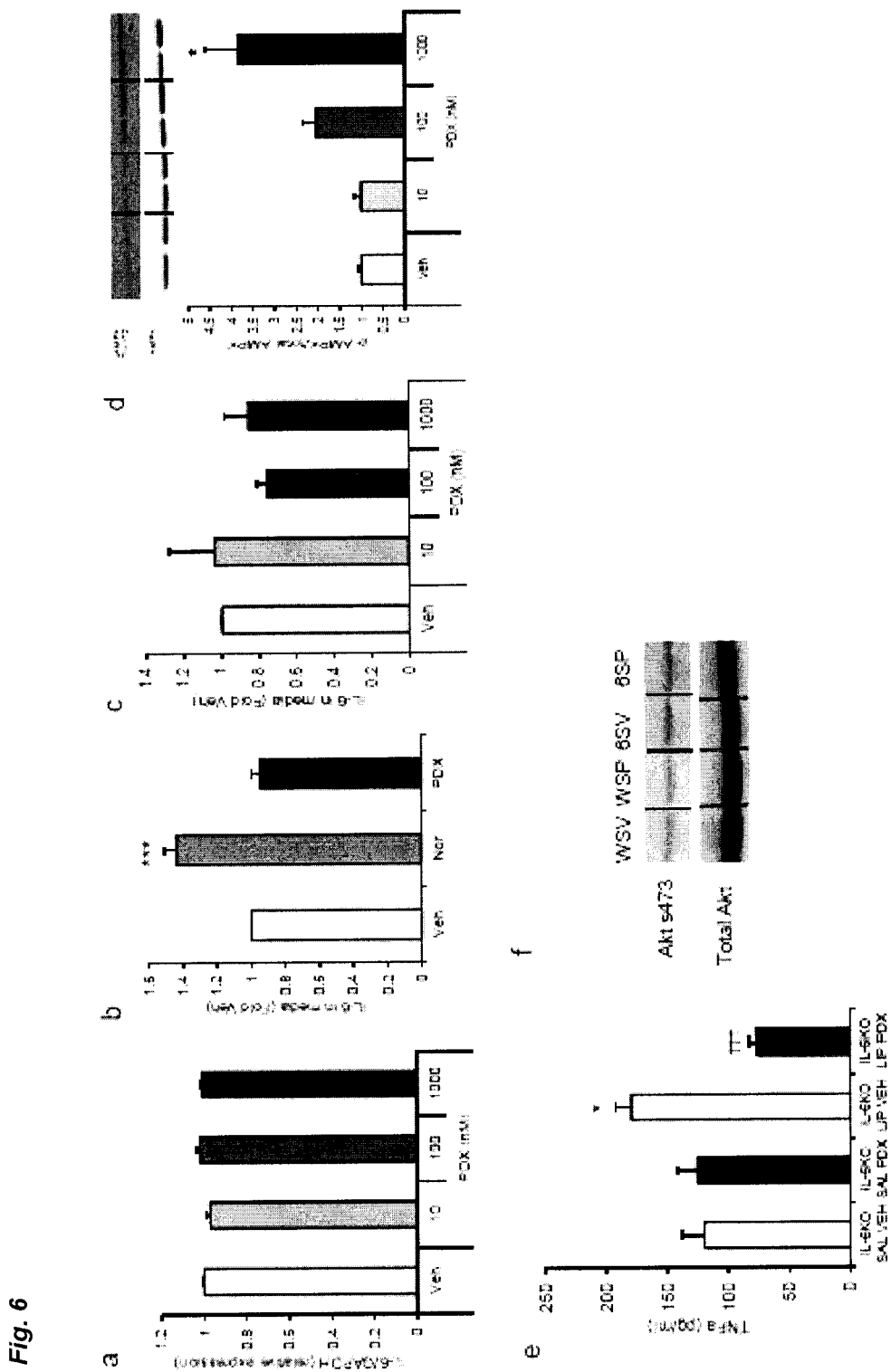

FIG. 6. PDX does not induce IL-6 mRNA expression in cultured macrophages

Figure 7:
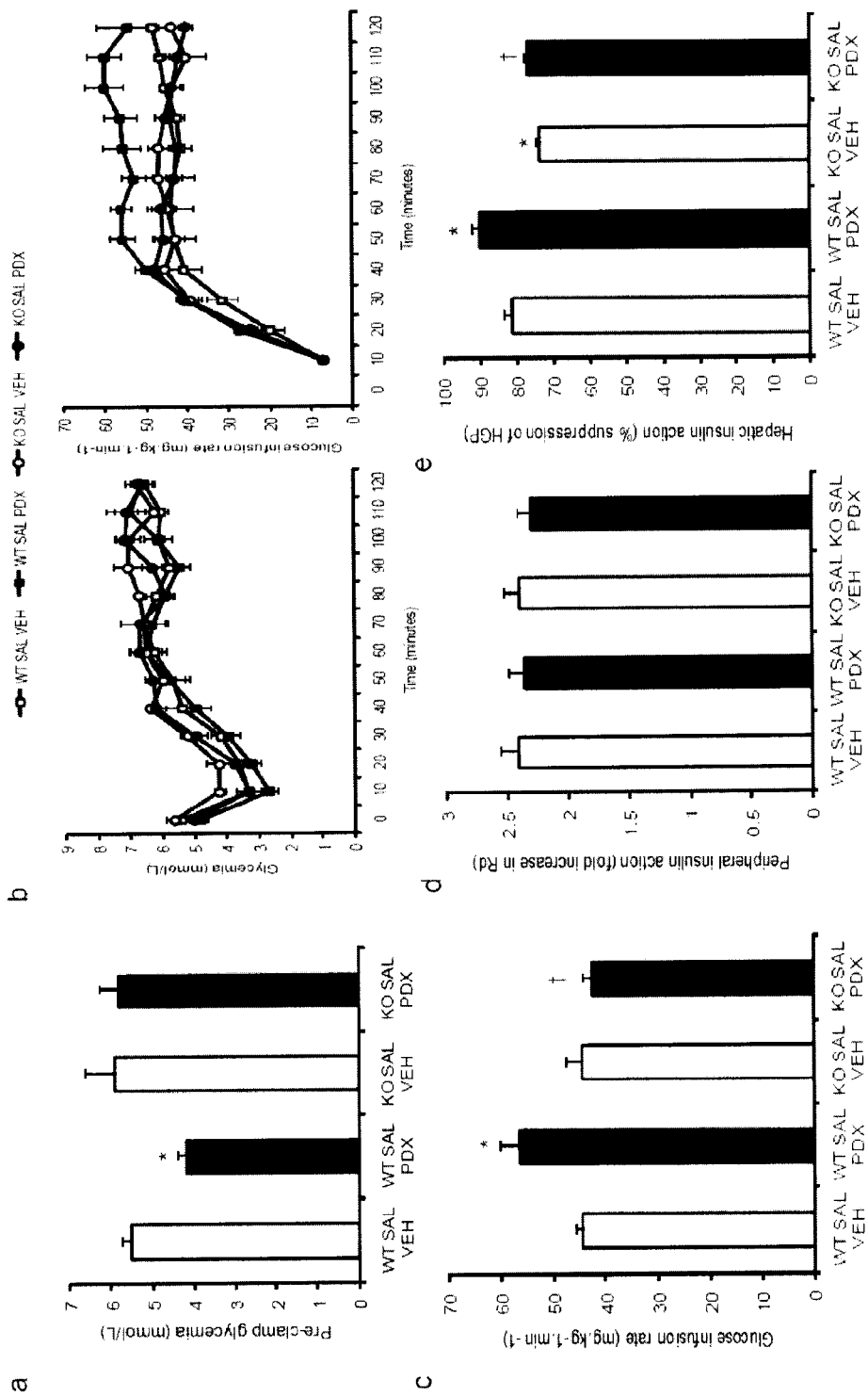
Figure 7:
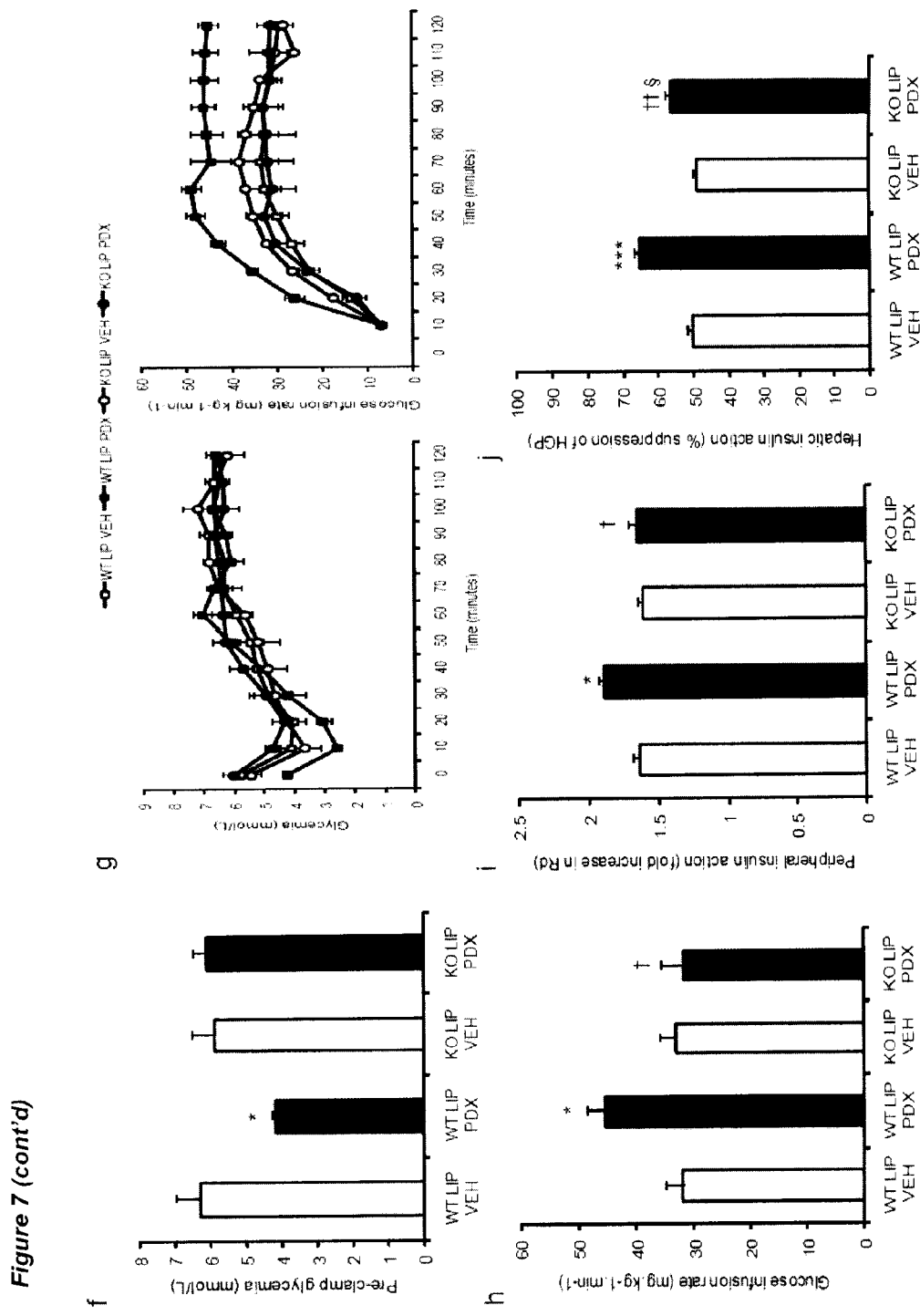

FIG. 7. IL-6 is required for the insulin sensitizing actions of PDX

Pre-clamp glycemia for PDX and vehicle (VEH) treated saline-infused animals are shown in panel a. (b) Glycemia and GIR during the hyperinsulinemic-euglycemic clamp. (c) Mean GIR for last 60 min of clamp is improved by PDX administration in C57BL/6J (WT) but not IL-6 null (KO) mice. (d-e) Peripheral and hepatic insulin action in saline-infused animals during the clamp. (f) Pre-clamp glycemia for PDX and VEH treated lipid-infused animals. (g) Glycemia and GIR during the clamp. (h) Mean GIR for last 60 min of clamp is improved by PDX in WT but not KO mice. (i-j) Peripheral and hepatic insulin action in lipid-infused animals during the clamp. All data are mean±SEM, n=5-8 *$P<0.05$, ***$P<0.001$ vs WT VEH; †$P<0.05$, ††$P<0.01$ vs WT PDX; §$P<0.05$ vs KO VEH.

Figure 8:
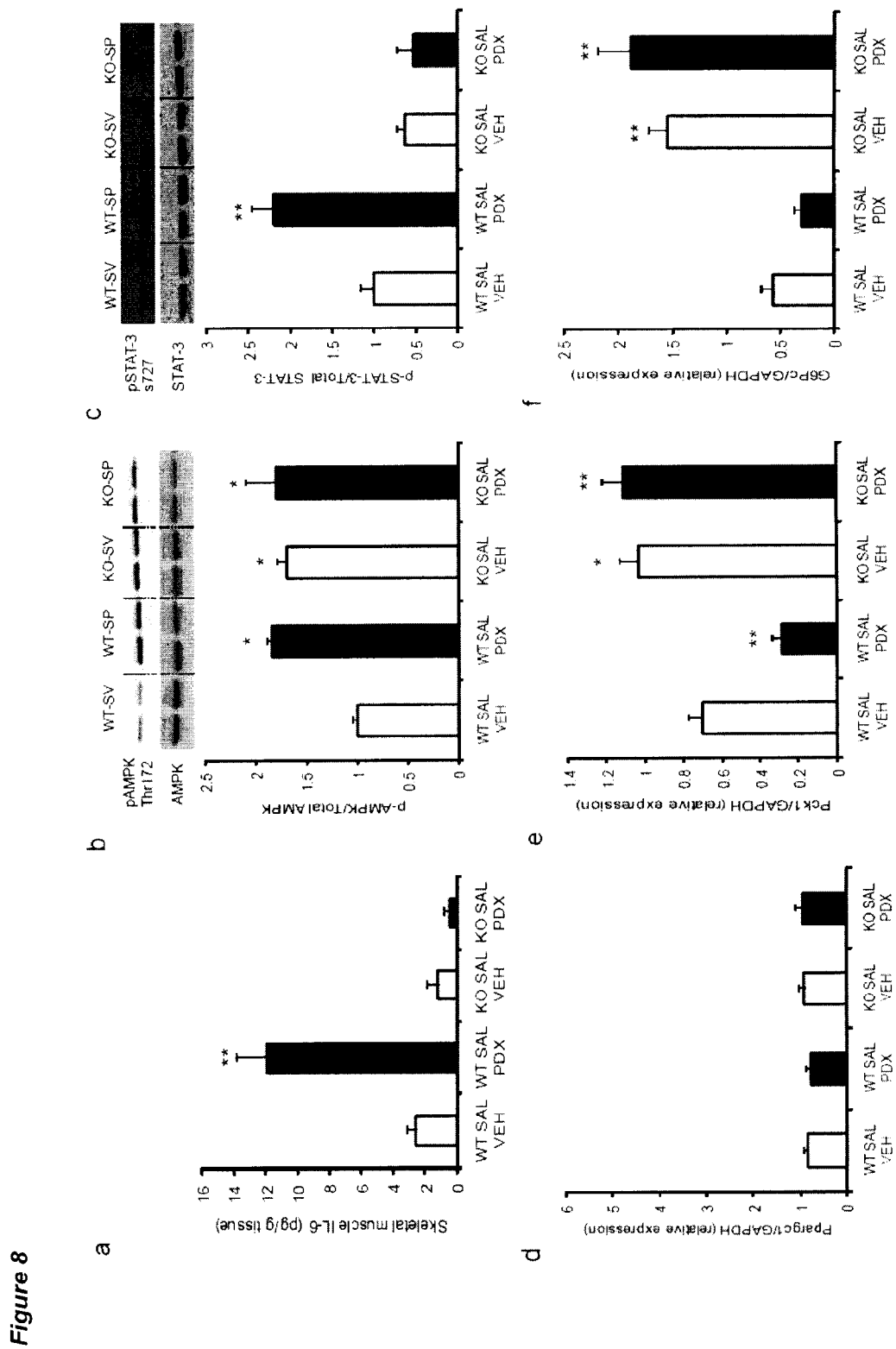
Figure 8:
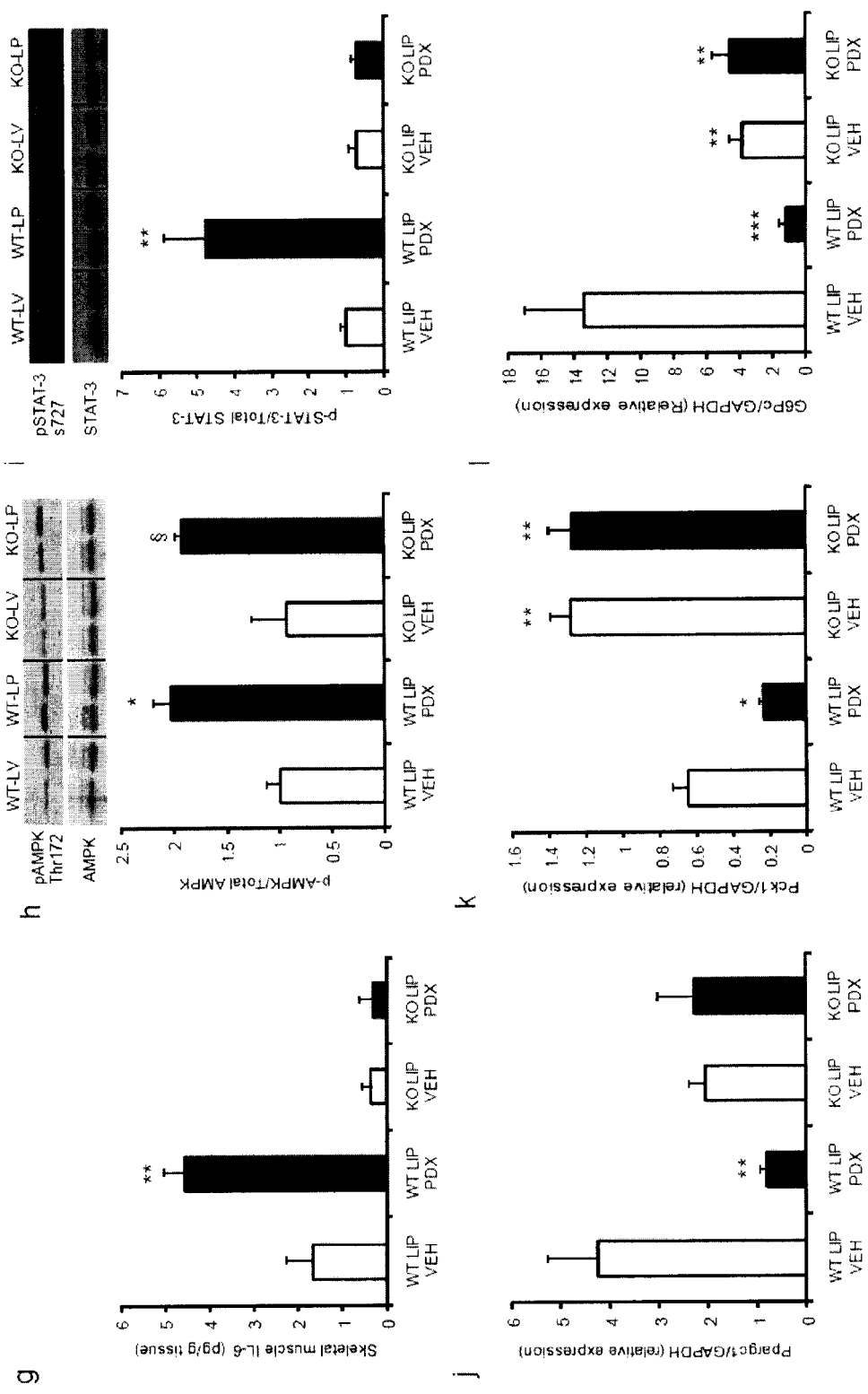

FIG. 8. Role of IL-6 in PDX mediated activation of AMPK and STAT-3

Panel a shows IL-6 protein expression in skeletal muscle of PDX and vehicle (VEH) treated saline-infused animals. (b-c) Immunoblots for pAMPK thr172/total AMPK in muscle and pSTAT-3 ser727/total STAT-3 in liver. (d-f) Relative mRNA expression for Ppargc1, Pck1 and G6Pc. (g) IL-6 protein expression in skeletal muscle of PDX and vehicle (VEH) treated lipid-infused animals. (h-i) Immunoblots for pAMPK thr172/total AMPK in muscle and pSTAT-3 ser727/total STAT-3 in liver. (j-l) Relative mRNA expression for Ppargc1, Pck1 and G6Pc. For all immunoblots quantification of densitometry analyses are shown below the representative gels. In each case lanes were run on the same gel but were noncontiguous. For all real-time RT-PCR data genes of interest were normalized to GAPDH using the delta delta CT method. All data are mean±SEM, n=5-8, *$P<0.05$, $P<0.01$, *$P<0.001$ vs WT VEH; §$P<0.05$ vs KO VEH.

Figure 9:
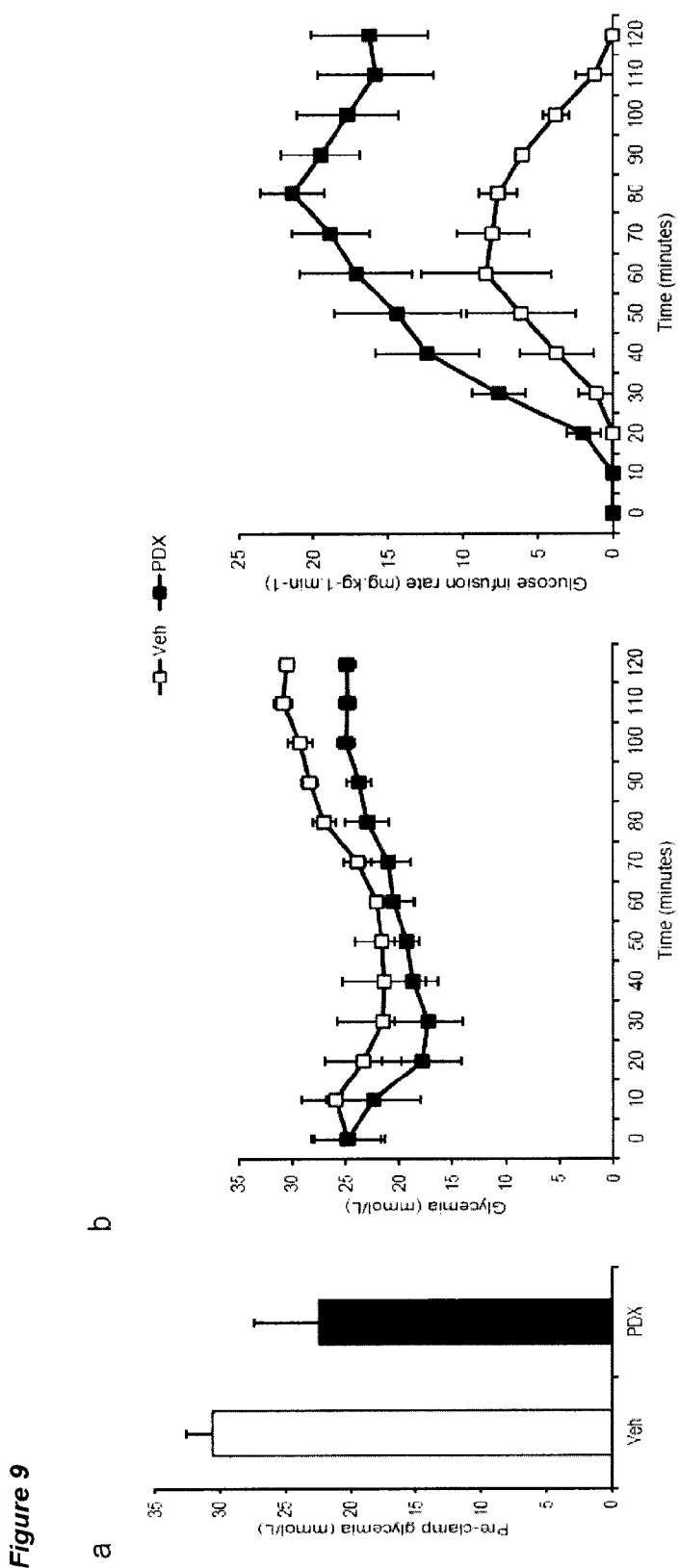
FIGS. 9a-9m. PDX therapy improves insulin sensitivity in diabetic mice
Figure 9:
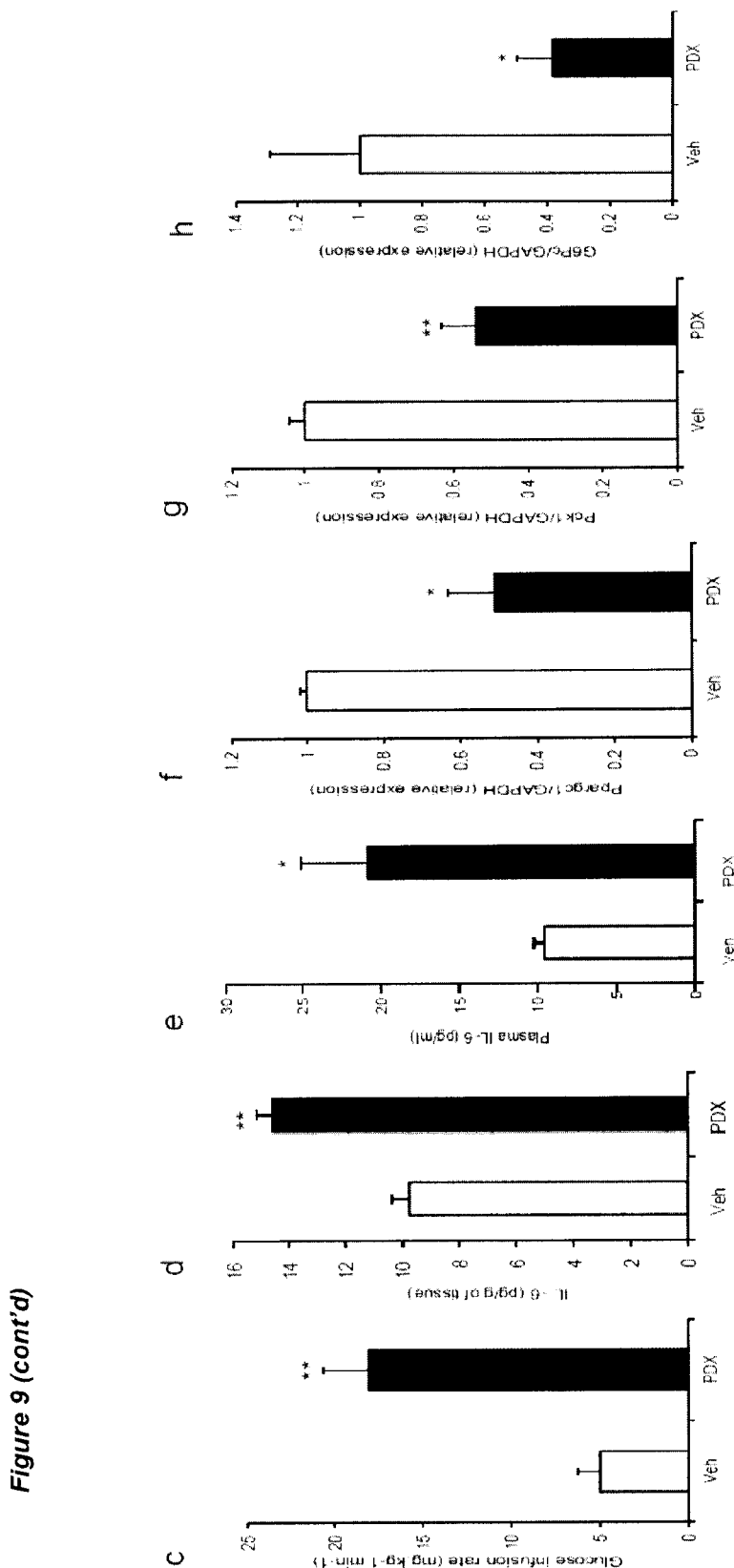
Figure 9:
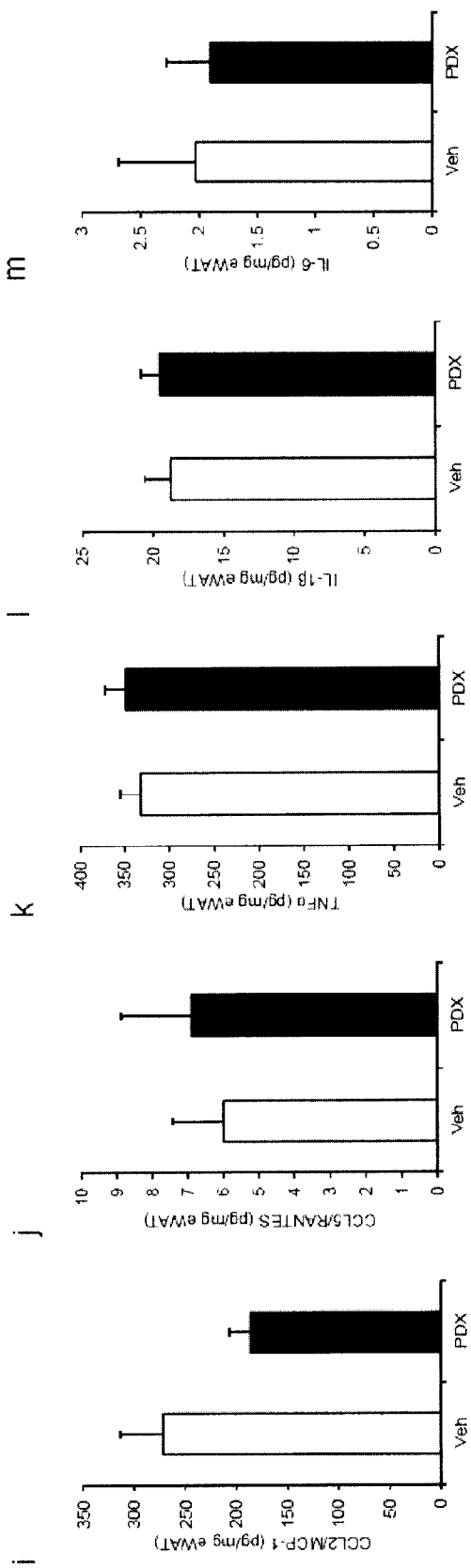

FIG. 9. PDX therapy improves insulin sensitivity in diabetic mice

Panel a shows pre-clamp glycemia in vehicle (Veh) and PDX treated genetically obese diabetic db/db mice. (b) Glycemia and GIR during the hyperinsulinemic-isoglycemic clamp. (c) Mean GIR for last 60 min of clamp is improved by PDX administration. (d) PDX increases skeletal muscle IL-6 protein expression. (e) PDX raises plasma IL-6 (f-h) PDX enhances the suppression of Ppargc1, Pck1 and G6Pc mRNA in liver. (i-m) PDX does not influence chemokines and cytokines in epididymal adipose tissue od db/db mice. All data are mean±SEM, n=3-4, *P<0.05, **P<0.01 vs Veh.

Figures 10, 11:
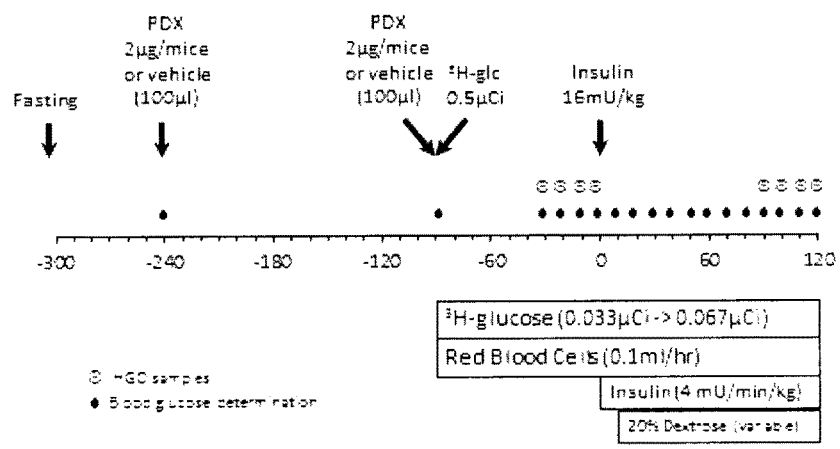
FIG. 10. Protocol for long term administration of PDX to db/db mice
FIG. 11. Schematic representation of the hyperinsulinemic-isoglycemic clamp procedure for the long-term administration of PDX FIG. 12. Total body weight and tissue weight in db/db mice during a 5 days PDX treatment FIGS. 13a-13l. Blood glucose and IL-6 levels in mice.

FIG. 10. Protocol for long term administration of PDX to db/db mice

FIG. 11. Schematic representation of the hyperinsulinemic-isoglycemic clamp procedure for the long-term administration of PDX FIG. 12. Total body weight and tissue weight in db/db mice during a 5 days PDX treatment FIG. 13. (a) Fasting blood glucose in 5 days PDX treated db/db mice. (b-e) Blood glucose levels and glucose infusion rate (GIR) during the clamp procedure. (f-I) IL-6 levels in gastrocnemius muscle and epididimal white adipose tissue (eWAT), as well as cytokines content of the eWAT.

ABBREVIATIONS AND DEFINITIONS

Abbreviations
ACC: Acetyl-CoA carboxylase; AMPK: Adenosine monophosphate-activated protein kinase; FFA: free fatty acid; HIE: hyperinsulinemic-euglycemic (clamp); GIR: glucose infusion rate; HGP: hepatic glucose production; iNOS: inducible nitric oxide synthase; JNK: c-Jun N-terminal Kinase; KO: nul or knock-out; pAMPK (phosphorylated) Adenosine monophosphate-activated protein kinase; VEH: vehicle; Rd: disappearance rate; RvD1L Resolvin D1; RvE1: Resolvin El; STAT-3: Signal transducer and activator of transcription 3; eWAT: epididimal white adipose tissue; iWAT: inguinal white adipose tissue; and WT: wild type.

Definitions
As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

The term "about" as used herein refers to a margin of + or −10% of the number indicated. For sake of precision, the term about when used in conjunction with, for example: 90% means 90%+/−9% i.e. from 81% to 99%. More precisely, the term about refer to + or −5% of the number indicated, where for example: 90% means 90%+/−4.5% i.e. from 86.5% to 94.5%.

Detailed Description Of Particular Embodiments
Use/Method for Increasing Secretion/Expression of Muscular IL-6

A use or a method for the treatment of a condition treated by the secretion of muscular IL-6 comprising the administration of an effective amount of PDX in a subject suffering therefrom.

Lowering Blood Glucose
Particularly, the use or the administration of a molecule in accordance with the method of the invention allows for the lowering of blood glucose in a subject.

Increasing Glucose Absorption
Particularly, the use or the administration of a molecule in accordance with the method of the invention allows for increasing body or skeletal muscle glucose absorption.

Exercise Recovery
Alternatively, the invention provides a use/a method for stimulating muscular IL-6 secretion during strenuous effort, thereby facilitating recovery of energy sources post-exercise.

Increased Energy During Effort
An alternative embodiment of the use/the method of the invention provides a way for increasing energy supply during effort involving increased secretion of muscular IL-6 during the exercise.

Specific Molecules
Particularly, in connection with the above-mentioned methods, the molecule used or administered is Protectin DX (PDX). Specifically, Protectin DX is also known as 10S, 17S-dihydroxy-docosa-4Z,7Z,11E,13Z,15E,19Z-hexaeonic acid:

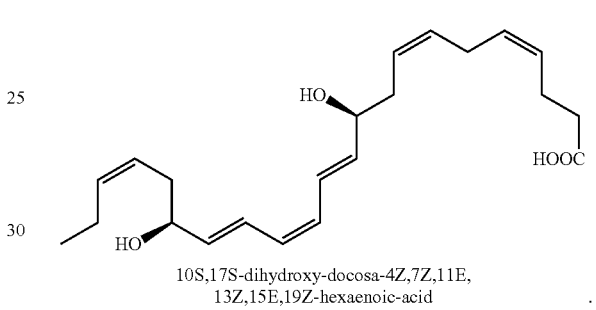

10S,17S-dihydroxy-docosa-4Z,7Z,11E,
13Z,15E,19Z-hexaenoic-acid

Conditions/Disorders
In connection with the uses/methods of the present invention, the administration of PDX, can effectively enhance or regulate blood glucose or lipid metabolism.

Alternatively, the condition being treatable by the method of the invention is an inflammatory condition.

Alternatively, the condition treatable by the method of the present invention is selected from the group consisting of: metabolic syndrome, insulin resistance, type 2 diabetes, cardiovascular disease, atherosclerosis, hypertension, arthritis, arthrosis, chronic fatigue syndrome, fibromyalgia and sarcopenia.

Still, alternatively, the use or method of the present invention can be useful for treating conditions such as exercise recovery or muscular fatigue, particularly in athletes, more particularly in high performance athletes.

Mode of Administration
In accordance with a particular embodiment of the invention, the method is carried out in accordance with the different aspects defined herein, wherein the administration is performed by different routes such as, for example: intravenous, oral, intranasal, subcutaneous or transcutaneous (i.e. patch).

Formulation
In accordance with the use of the present invention for the manufacture of a formulation, such formulation is adapted to be administered intravenously, orally, intranasally, subcutaneously or transcutaneously (i.e. patch).

Subject
In accordance with a particular embodiment of the invention, the use or method is carried out in accordance with the different aspects defined herein, wherein the subject is a mammal. Particularly, the mammal is a horse or a human. More particularly, the subject is a human.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

Example 1

Evaluation of PDX

Experimental Procedures
Animal Studies 14-week old male C57BL/6J mice from Jackson Labs were used for the first paired lipid infusion hyperinsulinemic-euglycemic clamp study. These mice were placed on a standard laboratory chow diet with free access to food and water and kept in a 12 h light 12 h dark cycle at the Laval University hospital research centre animal facility. Mice were randomly assigned to saline, lipid or lipid+PDX groups. Five days prior to the experiment, mice were anesthetized and PE-10 catheters (Harvard Apparatus, QC, Canada) were inserted into the left common carotid artery and the right jugular vein for blood sampling and infusions respectively. Mice were fasted for 5 h leading up to the protocol. Immediately prior to the start of the lipid infusion, PDX (1 ug) or an equal volume of vehicle was administered via the jugular catheter to each group. Mice were then infused for 6 h with saline (5ml·kg$^{-1}$·h$^{-1}$) or lipid (20% intralipid emulsion (Baxter, ON, Canada) 5ml·kg$^{-1}$·h$^{-1}$ with 20 IU·ml$^{-1}$ heparin (LEO pharma, ON, Canada)). 2.5h into the infusion PDX (1 ug) or vehicle was again administered to the appropriate groups and the HIE clamp was initiated as previously described [8,27]. The clamp protocol consisted of a 90 min tracer equilibration period followed by a 120 min experimental period. A 5-μCi bolus of [3-$^3$H]glucose was given at the start of the tracer equilibration period followed by a 0.05-μCi/min infusion for 90 min. Blood samples were drawn for the assessment of glycemia, insulin and glucose turnover levels. Following the 90 min tracer equilibration period the clamp began with a primed-continuous infusion of human insulin (16 mU/kg bolus followed by 4 mU·kg$^-$$_1$·min$^{-1}$, Humulin R; Eli Lilly, Indianapolis, Ind.). The [3-$^3$H]glucose infusion was increased to 0.2 μCi/min for the remainder of the experiment. Euglycemia (6.0-7.0 mM) was maintained during clamps by infusing 20% dextrose as necessary. Blood samples were taken continuously to determine glucose specific activity as well as insulin concentrations. Mice received saline-washed erythrocytes from donor mice throughout the experimental period (5-6 μl·min-1) to prevent a fall of ≥5% hematocrit. HGP and Rd were determined using Mari's non-steady-state equations for a two-compartmental model[28].

For the second paired lipid infusion HIE clamp study, 10 week old male B6.129S2-Il6$^{tm1kopf}$/J (IL-6 KO) and control C57BL/6J (WT) mice from Jackson Labs were used. Mice from each genetic background were randomly assigned to saline-vehicle, saline-PDX, lipid-vehicle and lipid-PDX groups. The lipid-infusion clamp study was performed as described above, except the clamp was performed with a 2.5 mU·kg$^{-1}$·min$^{-1}$ insulin infusion as per[29].

The 4 mU/kg hyperinsulinemic-isoglycemic clamp study was performed in 10 week old db/db mice from the BKS.Cg-Dock7$^m$+/+Lepr$^{db}$/J strain at Jackson Labs. Mice were randomly assigned to vehicle or PDX treatment groups. In preparation for the clamps mice were catheterized as described for the lipid infusion study. Mice were administered 2 ug of PDX or an equal volume of vehicle i.v. at 4 h and also 90 minutes prior to the initiation of the insulin pump. Pre-clamp glycemia was taken immediately prior to the second PDX shot. The clamp began 90 minutes later with a primed-continuous infusion of human insulin (16 mU/kg bolus followed by 4 mU·kg$^{-1}$·min$^{-1}$, Humulin R; Eli Lilly, Indianapolis, Ind.). Glycemia was maintained as close as possible to individual fasting values by infusing 20% dextrose as necessary. Blood samples were taken continuously to determine glycemia as well as insulin concentrations. Mice received saline-washed erythrocytes from donor mice throughout the experimental period (5-6 μl·min-1) to prevent a fall of ≥5% hematocrit.

All animal procedures were approved and carried out in accordance with directions of The Laval University and Canadian Councils for Animal Care.

C2C12 Myotubes

C2C12 myoblasts were maintained in DMEM containing 10% FBS. Differentiation to myotubes was initiated by addition of DMEM containing 2% horse serum. The experiment was conducted 5 days after the addition of the differentiation media. Immediately prior to the commencement of experiments fresh media was added to the cells. Then vehicle or PDX (10, 100, and 1000 nM) was added to the appropriate wells. 30 and 120 minutes after the addition of PDX media was collected and frozen for IL-6 quantification and cells were washed in ice cold PBS. For extraction of mRNA cells were then lysed and scraped in 300 μl of RLT buffer (QIAGEN). For examination of AMPK activity cells were lysed and scraped in 200 μl of ice cold lysis buffer containing 50 mM HEPES pH7.5, 150 mM NaCl, 1 mM EGTA, 20 mM b-glycerophosphate, 1% NP40, 10 mM NaF, 2 mM Na3VO4, 1× protease inhibitor cocktail (Sigma).

Macrophages

J774A.1 murine macrophages were maintained in DMEM (10% FBS) until 80% confluence. A 2 mM palmitate solution or methanol vehicle in alpha-MEM (12% BSA) was added to fresh DMEM (10% FBS) to give a final concentration of 400 μM palmitate. Concomitantly, PDX, RvE1, RvD1 (10 or 100 nM, Cayman chemical), or vehicle was added to the media. After 16 hours, the media was collected and cells were lysed as described for the studies in C2C12 myotubes.

Western Blotting

Snap frozen gastrocnemius muscle and liver from mice were pulverized in liquid nitrogen then lysed overnight at 4° C. in the lysis buffer described for the C2C12 myotube experiments. Immunoblotting of myotube, macrophage, liver and muscle lysates was then performed as previously described[5]. Briefly, 50 ug of protein was loaded onto a 7.5% acrylamide gel, subjected to SDS-PAGE then transferred onto nitrocellulose membranes. Membranes were then blocked and probed with the appropriate antibodies. Antibodies for p-Akt ser473, p-JNK thr183/tyr185, JNK, p-AMPK thr172, AMPK, p-STAT-3 ser727 and STAT-3 were obtained from Cell Signaling Technology (MA, USA).

Antibodies for total Akt and iNOS were from Santa Cruz Biotechnology (CA, USA) and BD Transduction Laboratories™ (Canada) respectively.

Real-Time RT-PCR

RNA was extracted from C2C12 myotubes using an RNeasy® mini kit from QIAGEN. RNA from homogenized liver tissue was extracted using an RNeasy® fibrous tissue mini kit from QIAGEN. RNA was then reverse transcribed to cDNA using the high-capacity cDNA reverse transcription kit from applied biosystems. Real-time PCR for Ppargc1, Pck1, G6Pc, and GAPDH was then performed using Taqman assay on demand probes and primers from Applied Biosystems in a CFX96 real-time system from BIO-RAD. The relative expression of genes of interest was then determined by normalization to the housekeeping gene GAPDH using the comparative $C_T$ method for relative gene expression[30].

Analytical Methods

Chemokines and cytokines were quantified in macrophage media, or mouse plasma using the MILLIPLEX™ MAP mouse cytokine/chemokine kit (Millipore Corporation, MA, USA). Nitrite accumulation in media was determined by Greiss assay as previously described[25]. Plasma insulin levels were assessed by RIA (Linco, MI, USA). FFA were measured using an enzymatic colorimetric assay (Wako Chemicals, VA, USA). Skeletal muscle and liver IL-6 were quantified using the mouse IL-6 ELISA kit from R&D systems. Total plasma adiponectin was determined using the ELISA from ALPCO.

Statistical Analysis

A one-way ANOVA was used for data arising from saline and lipid infusion clamp studies as well as the in vitro studies in C2C12 myotubes and J774A macrophages. Bonferonni was the post-hoc test employed in each case. Students t-test was used to analyze data from the db/db clamps. In all cases results were considered significant when $P<0.05$.

Results

PDX prevents lipid-induced insulin resistance

We first evaluated the therapeutic potential of PDX for insulin resistance in the setting of lipid excess. Here we employed a 6h lipid infusion paired to a 4mU/kg hyperinsulinemic-euglycemic clamp in lean C57BL/6J mice (see design in FIG. 1)[8]. Lipid-infused mice were administered vehicle or PDX (1 ug i.v.) immediately prior to and 2.5 h into the 6 h lipid infusion. A saline-infused group was also clamped to ascertain baseline insulin sensitivity. Administration of PDX lead to a significant lowering of pre-clamp glycemia compared to both the saline and lipid-treated animals ($P<0.01$; FIG. 2a), suggesting that PDX directly modulates glucose metabolism. PDX treatment also completely prevented the lipid-induced decline in whole-body insulin sensitivity as determined by the glucose infusion rate (GIR) required to maintain euglycemia during the clamp ($P<0.001$; FIG. 2b-c). The improved insulin response in PDX-treated mice could be attributed to partial restoration of peripheral insulin action (FIG. 2d) and markedly increased hepatic insulin action which was actually significantly greater than that seen in saline-infused mice ($P<0.05$; FIG. 2e). Importantly, phosphorylation of Akt on Ser473 confirmed the improved insulin action in both liver and skeletal muscle of PDX treated mice (FIG. 2f-g).

PDX Inhibits Lipid-Induced Inflammation

To further explore the mechanism whereby PDX improves insulin sensitivity in the setting of lipid excess we next examined its influence on two established inflammatory mediators of insulin resistance, inducible nitric oxide synthase (iNOS)[9] and c-Jun N-terminal Kinase (JNK)[10]. In line with the classical role of protectins in the active resolution of inflammation, we found that PDX represses lipid-mediated induction of iNOS in both muscle and liver (FIG. 3a-b) and prevents JNK activation, as determined by phosphorylation on Thr183/Tyr185, in liver (FIG. 3c).

Since PDX effectively blunted the activation of these two well established inflammatory mediators of insulin resistance we next tested whether this was due to upstream inhibition of chemokine and cytokine secretion. We observed that PDX strongly suppresses lipid-induced secretion of the proinflammatory chemokines CCL2/MCP-1 and CCL5/RANTES (FIG. 3d-e) as well as the cytokines TNFα, IFNγ, IL-1β, IL-2 and IL-17 (FIG. 3f-j). However, surprisingly, in contrast to its effect on all other chemokines and cytokines tested, PDX actually promoted a ~7 fold increase in IL-6 beyond that induced by lipid infusion alone ($P<0.001$; FIG. 3k). These findings provide strong evidence that PDX is a potent inhibitor of lipid-induced inflammation but also suggest that the mechanism of action of PDX is more complex than first anticipated.

Since macrophages are important contributors to global chemokine and cytokine production we next examined whether PDX has the same influence in macrophages treated with palmitate in vitro. Here we observed that PDX effectively suppresses lipid-induced secretion of CCL2/MCP-1, CCL5/RANTES, TNFα, IL-2, and IL-10 as well as iNOS and JNK activation supporting our finding in lipid-infused mice (FIG. 4). However, rather than stimulating IL-6 release, here we found that PDX actually suppresses lipid-induced IL-6 production in macrophages (FIG. 4e). These data suggest that the marked rise in circulating IL-6 in PDX treated mice is likely derived from an alternate cellular source.

PDX Promotes IL-6 Expression in Skeletal Muscle

Since IL-6 was identified as the prototypic 'myokine' (muscle derived cytokine)[11,12] we felt that skeletal muscle could be the site of IL-6 release in PDX treated animals. We therefore examined IL-6 protein expression in skeletal muscle and also liver. Here we observed that the expression profile of IL-6 protein in muscle closely resembled that of plasma whereas no significant effect of PDX was observed on liver IL-6 levels (FIG. 5a-b). These data suggest that skeletal muscle is the likely source of IL-6 in PDX treated mice.

Since IL-6 was recently reported to underlie the insulin sensitizing actions of adiponectin in liver[13] we felt it was also important to determine whether PDX affected circulating adiponectin levels in our study. Here we found that adiponectin does not account for the PDX-mediated rise in circulating and skeletal muscle IL-6 since both lipid-infused groups displayed similarly reduced levels of adiponectin in plasma (FIG. 5c).

PDX Activates AMPK in Skeletal Muscle and STAT-3 in Liver

To ascertain whether IL-6 potentially contributes to the glucoregulatory and insulin sensitizing actions of PDX we next examined known metabolic targets of IL-6 in skeletal muscle and liver. IL-6 is thought to enhance glucose metabolism in muscle by activating AMP-activated protein kinase (AMPK)[14,15,16] and to regulate hepatic glucose production in liver via STAT-3 mediated transcriptional suppression of the gluconeogenic genes PGC-1α, PEPCK and G6Pase[17,18]. Accordingly, here we observed that PDX promotes robust phosphorylation of AMPK on Thr172 in muscle ($P<0.05$; FIG. 5d) while enhancing the phosphorylation of hepatic STAT-3 on Ser727 ($P<0.05$; FIG. 5e) and the suppression of PGC-1α and PEPCK in liver (FIG. 5f-g). There was also a tendancy for improved suppression of G6Pase in PDX treated animals but this did not reach significance (P=0.08; FIG. 5h).

PDX Promotes IL-6 Expression and Release in Cultured Myotubes

To confirm that PDX induces IL-6 expression and release from muscle in a cell-autonomous fashion we next treated cultured C2C12 myotubes with PDX. Here we observed that PDX stimulates a dose-dependant rise in IL-6 mRNA expression and accumulation in media within 2 h of administration with the highest dose promoting a more than 2-fold increase in IL-6 secretion and mRNA expression ($P<0.01$; FIG. 5i-j). We also detected phosphorylation of AMPK at this timepoint ($P<0.05$; FIG. 5k).

To determine the specificity of muscle IL-6 release for PDX's structure
(10(S),17(S), Dihydroxy 4Z,7Z,11E,13Z,15E,19Z Docosahexaenoic acid):

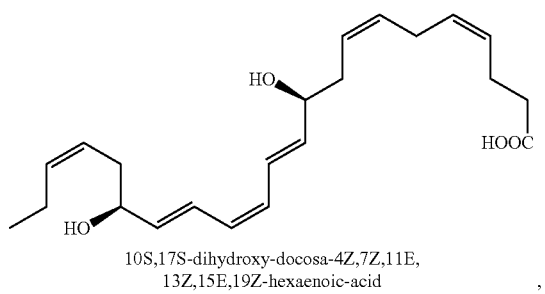 [SMILES: CC/C=C\C[C@H](O)/C=C/C=C\C=C\[C@@H](O)C/C=C\C/C=C\CCC(=O)O]

10S,17S-dihydroxy-docosa-4Z,7Z,11E,
13Z,15E,19Z-hexaenoic-acid , we next compared the potential of three structurally similar lipid mediators:
PD1 (10(S),17(S), Dihydroxy 4Z,7Z,11E,13Z,15E,19Z Docosahexaenoic acid):

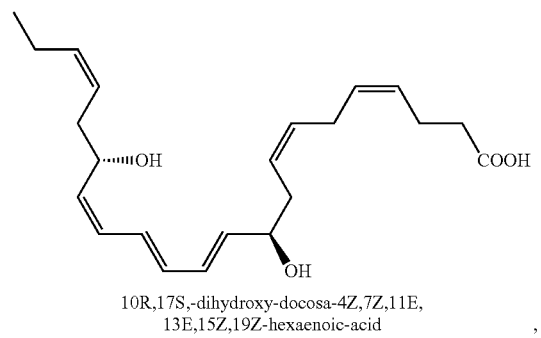 [SMILES: CC/C=C\C[C@H](O)\C=C/C=C/C=C/[C@H](O)C/C=C\C/C=C\CCC(=O)O]

10R,17S,-dihydroxy-docosa-4Z,7Z,11E,
13E,15Z,19Z-hexaenoic-acid ,

8(S) 15(S) DiHETE (8S,15S-dihydroxy-5Z,9E,11Z,13E-eicosatetraenoic acid):

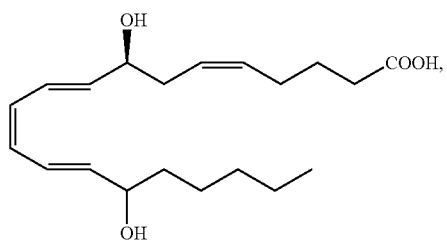 [SMILES: CCCCCC(O)/C=C/C=C\C=C\[C@@H](O)C/C=C\CCCC(=O)O]

or Resolvin D1 (RvD1; 7S,8R,17S-trihydroxy-4Z,9E,11E,13Z,15E,19Z-docosahexaenoic acid):

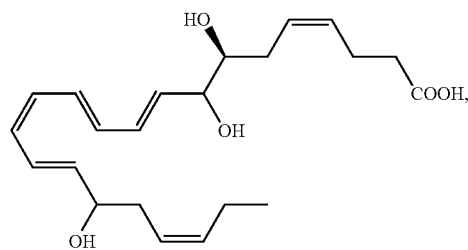 [SMILES: CC/C=C\CC(O)/C=C/C=C\C=C\C=C\C(O)[C@@H](O)C/C=C\CCC(=O)O]

to stimulate IL-6 release in C2C12 myotubes. Despite the presence of common structural features in each of these lipid mediators only administration of PDX prompted IL-6 release from muscle cells ($P<0.01$; FIG. 5l). Thus skeletal muscle IL-6 release appears to be a unique characteristic of PDX administration rather than a shared action of a novel lipid class.

In order to address the dichotomy in PDX's effect on IL-6 release from muscle versus macrophages, we next examined the impact of PDX on IL-6 release from cultured macrophages in the absence of palmitate stimulation (FIG. 5m). Here we found that while LPS clearly stimulates robust IL-6 release from these cells ($P<0.001$), PDX does not stimulate IL-6 release (FIG. 5m) or mRNA expression (FIG. 6a). Interestingly, despite the lack of stimulatory effect on IL-6 release in macrophages PDX was found to promote AMPK phosphorylation ($P<0.01$; FIG. 5n) as observed in C2C12 myotubes (FIG. 5k) and skeletal muscle taken from PDX treated mice (FIG. 5d). Since activation of AMPK represses inflammatory cytokine production in macrophages[19] this may explain the opposing effect of PDX on IL-6 expression and release in skeletal myotubes and activated macrophages.

Since brown adipose tissue was recently shown to regulate glucose homeostasis via secretion of IL-6[20] we also examined whether PDX might raise circulating IL-6 by stimulating brown fat. However, although cultured T37i brown adipocytes released IL-6 in response to adrenergic stimuli (norepinephrine 1 μM) we found that PDX was not able to stimulate the release of IL-6 from this cell type (FIG. 6b). Together these data identify PDX as a novel structurally distinct skeletal muscle IL-6 secretagogue and AMPK activator.

IL-6 is Required for the Beneficial Effects of PDX on Glucose Metabolism

To confirm the involvement of IL-6 in the beneficial effects of PDX we performed a second round of paired lipid infusion hyperinsulinemic-euglycemic clamp studies in IL-6 null (KO) mice alongside wild-type (WT) C57BL/6J control mice. Saline-infused mice treated with PDX were added to the study to ascertain whether PDX also improves glucose metabolism in insulin-sensitive mice. To ensure detection of potential differences between insulin-sensitive saline-infused animals we performed 2.5mU/kg/min rather than 4 mU/kg/min clamps.

Once again PDX induced a significant fall in pre-clamp glycemia in WT mice, importantly this effect was present in both saline and lipid-infused WT mice but completely absent in their KO counterparts ($P<0.05$; FIG. 7a and f). PDX treatment also significantly enhanced the GIR in saline and lipid-infused WT mice ($P<0.05$) but this was not the case in KO animals (FIG. 7b-c and 7g-h). The improved insulin sensitivity witnessed in the WT PDX treated saline-infused mice was entirely the result of superior hepatic insulin action (P<0.05; FIG. 7d-e). In contrast, PDX improved both peripheral (P<0.05) and hepatic (P<0.001) insulin action in lipid-infused mice (FIG. 7i-j). Interestingly, whereas the effect of PDX on hepatic insulin action in saline-infused mice and peripheral insulin action in lipid-infused mice were completely absent in KO animals, the effect on hepatic insulin action in lipid-infused mice was only partially lost (FIG. 7j). These data suggest that IL-6 is entirely responsible for the beneficial effects of PDX in unchallenged insulin-sensitive animals but that another mechanism triggered by PDX, possibly its inherent anti-inflammatory activity, likely contributes to the improvement of hepatic insulin action during lipid challenge.

IL-6 is not Required for PDX Mediated Activation of AMPK

As expected PDX failed to raise IL-6 in skeletal muscle of saline and lipid-infused KO mice (FIGS. 8a and g); however, this was not associated with reduced levels of AMPK phosphorylation compared to WT PDX treated mice (FIGS. 8b and h). Importantly, we observed that the stimulatory effect of PDX on AMPK phosphorylation is fully maintained in lipid-infused KO animals, which in contrast to their saline-infused counterparts, display normal baseline levels of AMPK phosphorylation (FIG. 8h). In light of these data we reexamined the early timeline of PDX-mediated IL-6 release and AMPK activation in C2C12 myotubes. Here we found that PDX promotes AMPK phosphorylation within 30 minutes but no IL-6 release can be detected in the media at this timepoint (FIG. 6c-d). Together these data demonstrate that IL-6 is not required for PDX mediated activation of AMPK. Interestingly, in line with the anti-inflammatory action of AMPK, we also found that PDX maintained its ability to potently suppress lipid-induced elevations in circulating TNFa in IL-6 KO mice (P<0.001; (FIG. 6e). These data suggests that the anti-inflammatory actions of PDX are IL-6 independent and separate from the major glucoregulatory mechanisms of PDX PDX Regulates the STAT-3-Gluconeogenesis Axis in an IL-6 Dependent Manner We next evaluated the role of IL-6 in PDX-mediated activation of hepatic STAT-3 and the transcriptional suppression of hepatic gluconeogenesis. Importantly, in contrast to AMPK and TNFα, this effect of PDX was found to be completely absent in KO mice (FIGS. 8c and i). The activation of STAT-3 by PDX was not associated with further suppression of PGC-1α in insulin-sensitive saline-infused mice (FIG. 8d). However, PDX administration clearly had an additive effect on the transcriptional repression of PEPCK downstream of PGC-1α (P<0.01, FIG. 8e). Importantly, this effect of PDX was found to be completely absent in saline-infused KO mice. PDX administration also tended to improve the suppression of G6Pc in saline-infused WT mice (P=0.0614; FIG. 8f) but this was not the case for their KO counterparts. It is noteworthy that the expression of PEPCK and G6Pc in KO mice was higher than in vehicle treated WT mice (FIG. 8e-f), consistent with the reduced hepatic insulin action in these mice (FIG. 7e).

In contrast to the insulin-sensitive saline-infused mice, PDX administration significantly improved the suppression of Ppargc1 (P<0.01) alongside Pck1 (P<0.05) and G6Pc (p<0.001) in lipid-infused WT mice (FIG. 8j-l). Importantly, these effects of PDX were entirely absent in lipid-infused KO mice. As observed for saline-infused mice, systemic absence of IL-6 lead to an increase in Pck1 expression compared to vehicle treated WT mice (P<0.01, FIG. 8k); however, this was not the case for G6Pc whose expression was significantly reduced compared to vehicle treated WT mice (P<0.01, FIG. 8l). The discrepant effect of IL-6 deficiency on Pck1 and G6Pc expression may explain the lack of further deterioration of hepatic insulin action in lipid-infused KO mice (FIG. 7j).

It is noteworthy that PDX improved the inhibition of hepatic glucose output and suppression of gluconeogenic enzymes in insulin sensitive saline infused mice without raising Akt phosphorylation (FIG. 6f) suggesting that the hepatic STAT-3 axis is the major pathway responsible for the glucoregulatory effects of PDX.

PDX Therapy Improves Insulin Sensitivity in Diabetic Mice

We further explored the therapeutic efficacy of PDX in genetically obese db/db mice, a well-established model of T2D. Here we tested the ability of PDX to rapidly alleviate insulin resistance using a 4 mU/kg hyperinsulinemic-isoglycemic clamp (see design in FIG. 1). In these experiments, db/db mice were treated with vehicle or PDX (2 µg i.v.) 240 and 90 minutes prior to the initiation of the clamp. As observed in lipid-infused C57BL/6J mice, PDX tended to lower pre-clamp glycemia but this effect did not reach statistical significance in these severely diabetic mice (FIG. 9a). However, PDX treatment very significantly improved insulin sensitivity, as revealed by a 3.6-fold improvement of the GIR during the clamp (P<0.01; FIG. 9b-c). Accordingly, PDX treatment enhanced suppression of PGC-1α, PEPCK, and G6Pase mRNA expression in liver (FIG. 9e-g). Importantly, as observed in the earlier studies, PDX treatment increased IL-6 in the skeletal muscle and plasma of db/db mice (P<0.01; FIG. 9d). Interestingly, these beneficial effects occurred in the absence of any significant anti-inflammatory impact of PDX on adipose tissue chemokines or cytokines (FIG. 9 i-m).

Example 2

Long-Term Efficacy

In order to determine whether these beneficial effects of PDX could be sustained or improved with a prolonged treatment regimen, we administered 2 µg of PDX or vehicle (i.v.) twice daily to 17 week old db/db for 5 days leading up to the clamp experiment (FIGS. 10 and 11).

The hyperinsulinemic-isoglycemic clamp (FIG. 11) is the gold-standard for evaluating insulin stimulated glucose metabolism in viva Animals were fasted around 8 am (t=−300 min), and received a first injection of either PDX (2 µg/mice) or the vehicle (10% Ethanol) at t=−240 min. A second injection was given at time −90 min, after which the clamp procedure per se was started. This procedure consisted of a 90-min tracer equilibration period (t=−90 to 0 min) followed by a 120 min hyperinsulinemic isoglycemic clamp (t=0 to 120 min). A 50 µl blood sample was obtained at t=−90 min to determine radioactive-free plasma activity. A 0.5 µCi bolus of [3-3H]-glucose was given at t=−90 min followed by a 0.033 µCi/min infusion for 90 min (t=−90 to 0 min). At t=−30, -20, -10 and 0 min, blood samples were taken for the assessment of basal glucose and glucose specific activity. The insulin infusion began at t=0 min with a primed-continuous infusion of human insulin (16 mU/kg bolus followed by a 4 mU/kg/min infusion), to achieve plasma insulin concentrations 2.5-fold over basal concentrations. At t=0 min, the [3-3H]-glucose infusion was increased to 0.066 µCi/min for the remainder of the experiment to minimize changes in specific activity from the equilibration period. Isoglycemia was maintained by measuring blood glucose every 10 min starting at t=0 min and infusing 20% glucose as necessary to preserved the blood glucose at basal levels. Blood samples were taken every 10 min from t=90 to 120 min for the determination of glucose specific activity.

Figure 12:
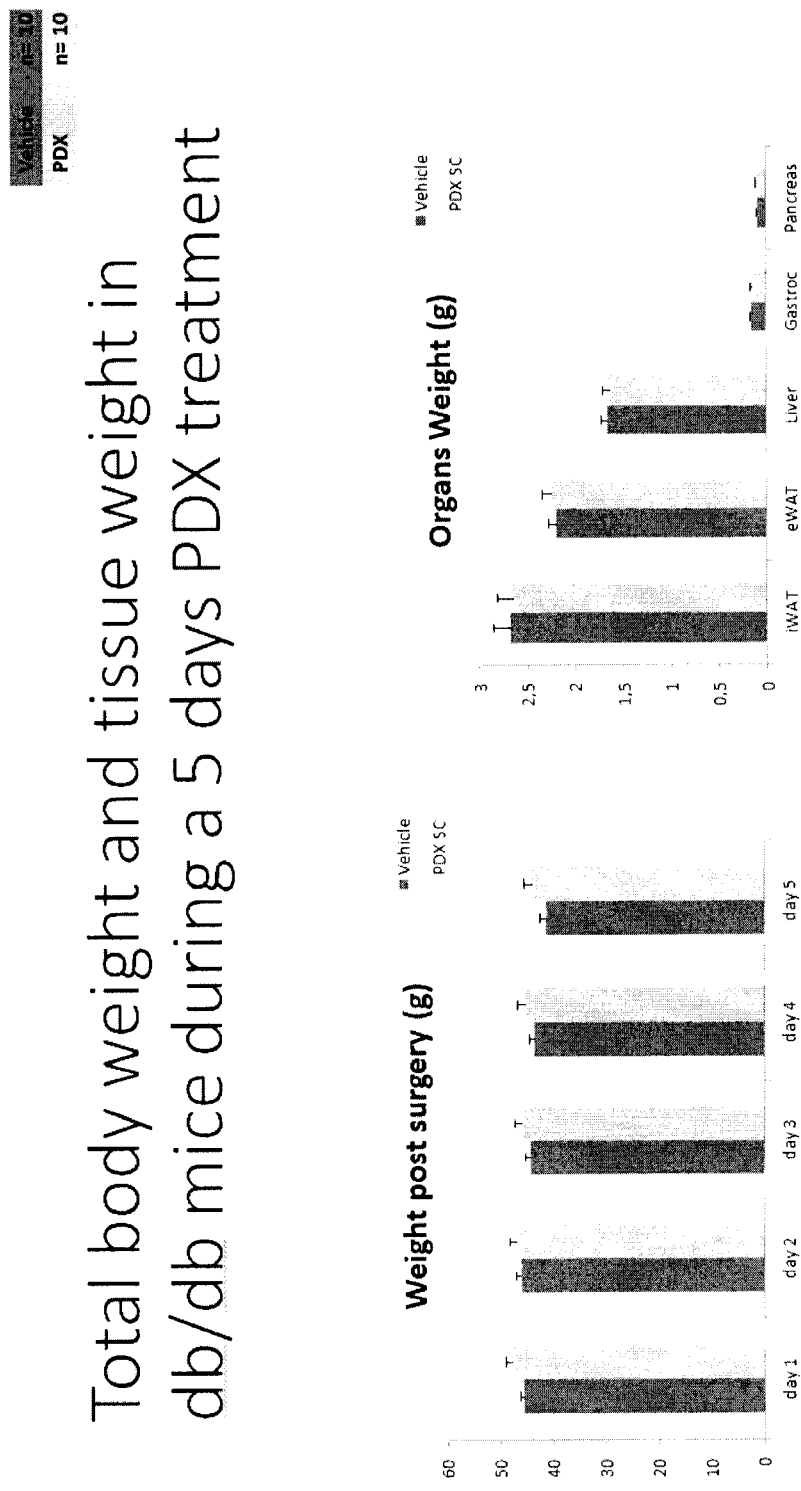
Figure 13:
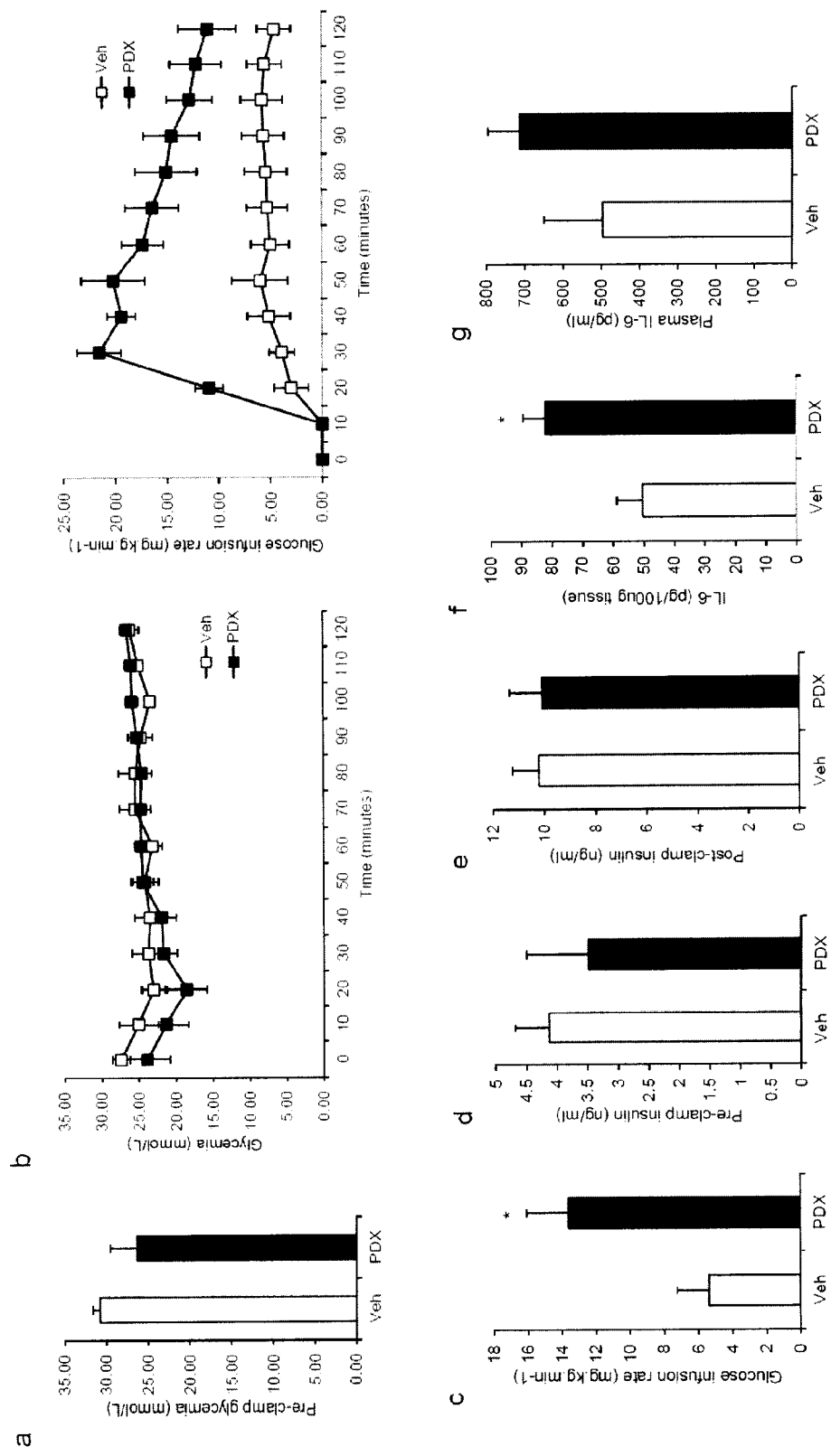
Figure 13:
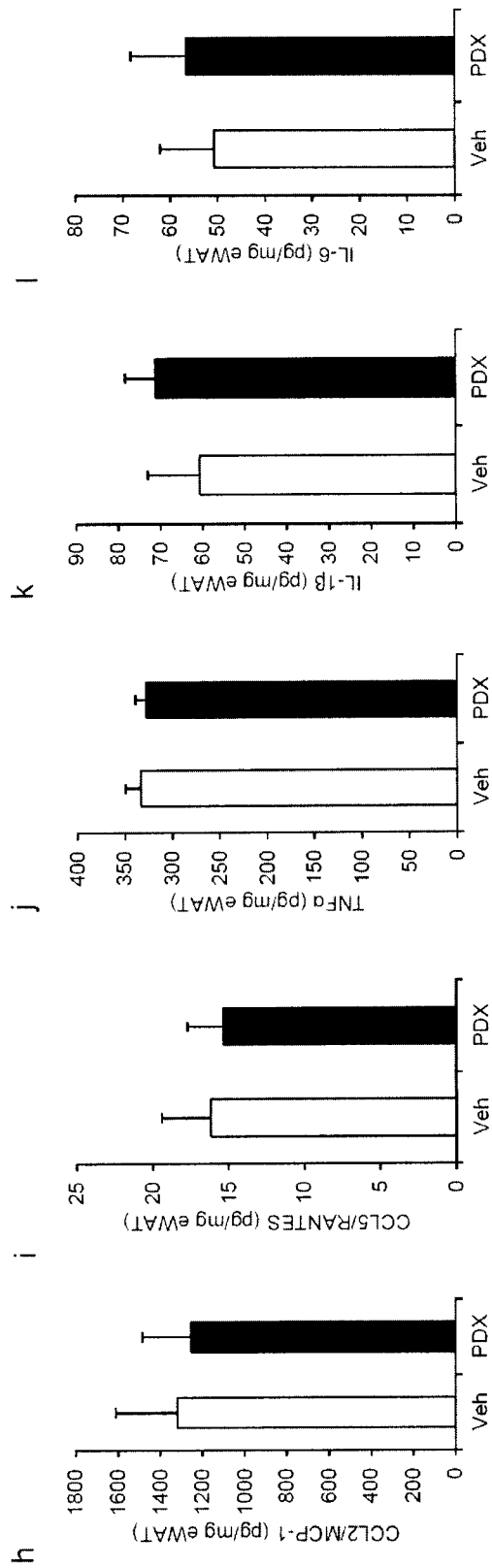

FIG. 12 shows that no significant changes was seen in total body weight during the 5 day treatment between the PDX-treated group and vehicle-treated group (left panel).

As well, the weight of different tissue taken at the end of the 5 days treatment. Tissues assessed were: inguinal and epididymal white adipose tissue (iWAT and eWAT), liver, gastrocnemius (skeletal muscle of the hind leg) and pancreas. No significant changes were observed (right panel). Therefore, a 5 days treatment with 2 μg of PDX per day did not affect total body weight or individual tissue weight.

As in the acute study PDX administration tended to lower glycemia; however, this did not reach significance in these severely obese diabetic mice (FIG. 13a). Therefore, fasting blood glucose and plasmatic insulin levels were not affected by a 5 day PDX treatment, neither was the insulin clearance.

Nonetheless the improved insulin sensitivity observed in db/db mice treated acutely with PDX was conserved in those mice treated with PDX for 5 days (FIG. 13b), since glucose levels were successful maintained at similar levels throughout the clamp procedure, especially during the critical period of the procedure (the last 60 min). This is an indication that the clamp procedure was properly conducted, and therefore comparison of the insulin responses can be made between the 2 groups.

Glucose infusion rate (GIR) is an indication of the whole body insulin sensitivity. An increase in GIR represent an increase in insulin sensitivity. Therefore, a clear improvement in insulin sensitivity was seen in db/db mice after the 5 days PDX treatment (FIG. 13c).

The improved insulin sensitivity observed was once again associated with elevated skeletal muscle IL-6 ($P<0.05$) and a trend for increased plasma IL-6 (FIG. 13f-g). Thus the effectiveness of PDX does not appear to dissipate with extended treatment.

Interestingly, lengthening the PDX treatment regime to 5 days was not sufficient to resolve inflammatory cytokine production in adipose tissue of these very obese diabetic mice (FIG. 13h-l). While a clear increase in IL6 levels was seen in the gastrocnemius of the PDX-treated animals, no such increase was seen in the eWAT. On the other hand, a range of cytokines content was assess in the eWAT, but no difference was seen between the PDX-treated and the vehicle-treated animals. Therefore, PDX treatment induced a skeletal muscle specific increase in IL6 content.

Thus the glucoregulatory IL-6-STAT-3 dependent axis of PDX action appears to be entirely responsible for the improved glucose utilization observed in these obese diabetic mice. These outcomes in a severe model of T2D further support the therapeutic potential of PDX for type-2 diabetes through its ability to induce muscle IL-6 expression.

Discussion

In the present study we identified the docosanoid resolution mediator, PDX, as a novel glucoregulatory agent with exciting potential for combating insulin resistance and type-2 diabetes (T2D) owing to a combination of potent anti-inflammatory, glucose-lowering and insulin-sensitizing actions. Surprisingly this anti-inflammatory mediator appears to stimulate glucose metabolism in vivo by promoting the release of the prototypic myokine, IL-6. To the best of our knowledge this is the first report of an agent that directly promotes skeletal muscle IL-6 expression and release. Indeed, only contraction/exercise has been reported to stimulate IL-6 expression and release from muscle and the field has been waiting for muscle IL-6 secretagogues to be discovered as the myokine is known to exert beneficial effects on glucose homeostasis[11,12]. The remarkable potency exhibited by PDX for the treatment of insulin resistance and T2D suggests that skeletal muscle IL-6 secretagogues could become an exciting new class of agents for T2D therapy. Further study of the mechanisms by which PDX promotes muscle IL-6 release is thus warranted.

In line with the currently described mechanisms of action of IL-6 in the literature, our findings support a model wherein PDX-dependent IL-6 release promotes the suppression of hepatic glucose production in an endocrine fashion via STAT-3 mediated transcriptional repression of PGC-1α, PEPCK, and G6Pase[17,18]. We also found that PDX stimulates AMPK in skeletal muscle but this action does not appear to require muscle IL-6 release. Since the favorable effect of PDX on skeletal muscle glucose metabolism was entirely absent but anti-inflammatory actions sustained in IL-6 null mice, it appears that AMPK likely contributes to the anti-inflammatory actions of PDX reported herein and probably accounts for the opposing effect of PDX on IL-6 release in macrophages and skeletal muscle cells.

Interestingly, we found that PDX did not increase peripheral glucose disposal in saline-infused mice whereas there was a substantial improvement of glucose uptake in their lipid-challenged counterparts. These data suggest that PDX-induced IL-6 likely improves muscle glucose metabolism by protecting against the lipid insult rather than by directly promoting glucose uptake in this tissue. In contrast, PDX administration clearly potentiated insulin-mediated suppression of hepatic glucose production in both lipid and saline-infused mice suggesting that PDX-induced IL-6 directly modulates glucose production in liver. Our studies in IL-6 null mice support this notion and point toward a mechanism previously described by Inoue et al[18] whereby STAT-3 restricts PEPCK and G6Pase expression independently of insulin-mediated suppression of PGC1α. Importantly, we found that PDX improves the insulin-mediated suppression of PGC1α in both lipid-challenged and diabetic db/db mice while also activating STAT-3-dependent suppression of PEPCK and G6Pase.

To the best of our knowledge this is the first report where IL-6 KO mice were studied using the hyperinsulinemic-euglycemic clamp in conditions of lipid excess. Although lipid infusion and palmitate treatment do increase systemic and macrophage IL-6 production, respectively, our findings do not support a role for IL-6 in the development of lipid-induced insulin resistance since we found that lack of IL-6 does not prevent insulin resistance in lipid-infused mice. To the contrary, we found that insulin-sensitive saline-infused IL-6 KO mice display a slight defect in hepatic insulin action that is associated with altered regulation of hepatic PEPCK and G6Pase but not PGC1α. However, this was apparently not sufficient to cause a significant change in whole-body glucose disposal. Our data thus join a growing body of work[13,14,21,22] that argues for a positive role of IL-6 in the regulation of glucose metabolism.

Interestingly, in addition to potentiating insulin action, PDX administration also induced a characteristic lowering of basal glycemia that was IL-6 dependent and preceded insulin administration in both saline and lipid-infused mice. This suggests that PDX and IL-6 might also represent promising therapeutic targets as insulin-independent glucose lowering agents. This finding is in agreement with work showing that exposure of mouse soleus to IL-6 and soluble IL-6 receptor increases glucose transport ex vivo[23] and with a recent study showing that the hypoglycemic response to endotoxemia is absent in IL-6 KO mice[24]. Importantly, our data suggest that this glucose lowering effect of PDX is dependent on IL-6 mediated activation of the hepatic STAT-3 pathway which independently suppresses the expression of PEPCK and G6Pase[18].

In addition to providing the first evidence of the insulin sensitizing and glucoregulatory actions of PDX this is also the first report demonstrating the powerful ability of PDX to suppress lipid-induced inflammation. Importantly, we observed that PDX inhibits lipid-induced secretion of pro-inflammatory chemokines and cytokines as well as activation of two well established inflammatory mediators of insulin resistance, iNOS and JNK, in macrophages in culture as well as skeletal muscle and liver in vivo. This is the first report in any setting documenting that PDX can inhibit iNOS and JNK. Although the precise mechanism underlying this anti-inflammatory activity remains to be fully defined, it is plausible that activation of AMPK might underlie part of the anti-inflammatory activity of PDX[25,26].

In conclusion, we have identified the docosanoid resolution mediator, PDX, as a novel agent that carries potent therapeutic potential for lipid-induced and obesity-linked insulin resistance. What is more we have unraveled an unanticipated mechanism of action whereby PDX enhances both hepatic and peripheral glucose metabolism in vivo by increasing the prototypic myokine IL-6.

Importantly, we demonstrated that the ability to stimulate skeletal muscle IL-6 release was not present in structurally similar bioactive lipids, namely PD1, RvD1, and 8(S),17(S) DiHETE but appears to be unique to PDX. These findings may lead to the development of muscle IL-6 secretagogues as a novel class of drugs that carry both anti-inflammatory and anti-diabetic actions.

REFERENCES

1. White, P. J. & Marette, A. Inflammation-Induced Insulin Resistance in Obesity: When Immunity Affects Metabolic Control in *Physical activity and type 2 diabetes: therapeutic effects and mechanisms of action* (eds. Hawley, J. A. & Zierath, J. R.) 83-106 (Human Kinetics, Champaign, Ill., 2008).
2. Wellen, K. E. & Hotamisligil, G. S. Inflammation, stress, and diabetes. *J Clin Invest* 115, 1111-1119 (2005).
3. Norling, L. V. & Serhan, C. N. Profiling in resolving inflammatory exudates identifies novel anti-inflammatory and pro-resolving mediators and signals for termination. *J Intern Med* 268, 15-24 (2010).
4. Kang, J. X., Wang, J., Wu, L. & Kang, Z. B. Transgenic mice: fat-1 mice convert n-6 to n-3 fatty acids. *Nature* 427, 504 (2004).
5. White, P. J., Arita, M., Taguchi, R., Kang, J. X. & Marette, A. Transgenic restoration of long-chain n-3 fatty acids in insulin target tissues improves resolution capacity and alleviates obesity-linked inflammation and insulin resistance in high-fat-fed mice. *Diabetes* 59, 3066-3073 (2010).
6. Serhan, C. N., et al. Anti-inflammatory actions of neuroprotectin D1/protectin D1 and its natural stereoisomers: assignments of dihydroxy-containing docosatrienes. *J Immunol* 176, 1848-1859 (2006).
7. Chen, P., et al. Full characterization of PDX, a neuroprotectin/protectin D1 isomer, which inhibits blood platelet aggregation. *FEBS Lett* 583, 3478-3484 (2009).
8. Charbonneau, A. & Marette, A. Inducible nitric oxide synthase induction underlies lipid-induced hepatic insulin resistance in mice: potential role of tyrosine nitration of insulin signaling proteins. *Diabetes* 59, 861-871 (2010).
9. Perreault, M. & Marette, A. Targeted disruption of inducible nitric oxide synthase protects against obesity-linked insulin resistance in muscle. *Nat Med* 7, 1138-1143 (2001).
10. Hirosumi, J., et al. A central role for JNK in obesity and insulin resistance. *Nature* 420, 333-336 (2002).
11. Pedersen, B. K. & Febbraio, M. A. Muscle as an endocrine organ: focus on muscle-derived interleukin-6. *Physiological reviews* 88, 1379-1406 (2008).
12. Pedersen, B. K. & Febbraio, M. A. Muscles, exercise and obesity: skeletal muscle as a secretory organ. *Nature reviews. Endocrinology* (2012).
13. Awazawa, M., et al. Adiponectin enhances insulin sensitivity by increasing hepatic IRS-2 expression via a macrophage-derived IL-6-dependent pathway. *Cell Metab* 13, 401-412 (2011).
14. Carey, A. L., et al. Interleukin-6 increases insulin-stimulated glucose disposal in humans and glucose uptake and fatty acid oxidation in vitro via AMP-activated protein kinase. *Diabetes* 55, 2688-2697 (2006).
15. Kelly, M., Gauthier, M. S., Saha, A. K. & Ruderman, N. B. Activation of AMP-activated protein kinase by interleukin-6 in rat skeletal muscle: association with changes in cAMP, energy state, and endogenous fuel mobilization. *Diabetes* 58, 1953-1960 (2009).
16. Kelly, M., et al. AMPK activity is diminished in tissues of IL-6 knockout mice: the effect of exercise. *Biochem Biophys Res Commun* 320, 449-454 (2004).
17. Inoue, H., et al. Role of hepatic STAT3 in brain-insulin action on hepatic glucose production. *Cell Metab* 3, 267-275 (2006).
18. Inoue, H., et al. Role of STAT-3 in regulation of hepatic gluconeogenic genes and carbohydrate metabolism in vivo. *Nat Med* 10, 168-174 (2004).
19. Sag, D., Carling, D., Stout, R. D. & Suttles, J. Adenosine 5'-monophosphate-activated protein kinase promotes macrophage polarization to an anti-inflammatory functional phenotype. *J Immunol* 181, 8633-8641 (2008).
20. Stanford, K. I., et al. Brown adipose tissue regulates glucose homeostasis and insulin sensitivity. *J Clin Invest* 123, 215-223 (2013).
21. Wunderlich, F. T., et al. Interleukin-6 signaling in liver-parenchymal cells suppresses hepatic inflammation and improves systemic insulin action. *Cell Metab* 12, 237-249 (2010).
22. Pedersen, B. K. & Febbraio, M. A. Point: Interleukin-6 does have a beneficial role in insulin sensitivity and glucose homeostasis. *J Appl Physiol* 102, 814-816 (2007).
23. Gray, S. R., Ratkevicius, A., Wackerhage, H., Coats, P. & Nimmo, M. A. The effect of interleukin-6 and the interleukin-6 receptor on glucose transport in mouse skeletal muscle. *Exp Physiol* 94, 899-905 (2009).
24. Tweedell, A., et al. Metabolic response to endotoxin in vivo in the conscious mouse: role of interleukin-6. *Metabolism* 60, 92-98 (2011).
25. Pilon, G., Dallaire, P. & Marette, A. Inhibition of inducible nitric-oxide synthase by activators of AMP-activated protein kinase: a new mechanism of action of insulin-sensitizing drugs. *J Biol Chem* 279, 20767-20774 (2004).
26. Centeno-Baez, C., Dallaire, P. & Marette, A. Resveratrol inhibition of inducible nitric oxide synthase in skeletal muscle involves AMPK but not SIRT1. *Am J Physiol Endocrinol Metab* 301, E922-930 (2011).
27. Xu, E., et al. Targeted disruption of carcinoembryonic antigen-related cell adhesion molecule 1 promotes diet-induced hepatic steatosis and insulin resistance. *Endocrinology* 150, 3503-3512 (2009).
28. Mari, A. Estimation of the rate of appearance in the non-steady state with a two-compartment model. *Am J Physiol* 263, E400-415 (1992).
29. Mulvihill, E. E., et al. Nobiletin attenuates VLDL overproduction, dyslipidemia, and atherosclerosis in mice with diet-induced insulin resistance. *Diabetes* 60, 1446-1457 (2011).
30. Schmittgen, T. D. & Livak, K. J. Analyzing real-time PCR data by the comparative C(T) method. *Nat Protoc* 3, 1101-1108 (2008).

The invention claimed is:

1. A method for increasing body or skeletal muscle glucose absorption in a subject in need thereof comprising administering to the subject in need an effective amount of Protectin DX (PDX) to increase body or skeletal muscle glucose absorption.

2. The method of claim 1, wherein said administration is performed by intravenous, oral, intranasal, subcutaneous or transcutaneous route.

3. The method of any one of claims claim 1, wherein said subject is a mammal.

4. The method of claim 3, wherein said mammal is a horse or a human.

* * * * *